US006277817B1

(12) United States Patent
Kruzel et al.

(10) Patent No.: US 6,277,817 B1
(45) Date of Patent: Aug. 21, 2001

(54) HUMAN LACTOFERRIN

(75) Inventors: Marian L. Kruzel, Houston, TX (US); Darrell J. Doyle, Blasdell, NY (US); Tomasz Kurecki, Lockport, WY (US); Paul D. Gollnick, Williamsville, NY (US)

(73) Assignee: Ferro Dynamics Inc., Houston, TX (US)

( * ) Notice: Subject to any disclaimer, the term of this patent is extended or adjusted under 35 U.S.C. 154(b) by 0 days.

(21) Appl. No.: 09/421,632

(22) Filed: Oct. 19, 1999

Related U.S. Application Data

(62) Division of application No. 08/724,586, filed on Sep. 30, 1996, now Pat. No. 6,066,469, which is a continuation of application No. 08/238,445, filed on May 5, 1994, now abandoned, which is a continuation-in-part of application No. 08/132,218, filed on Oct. 6, 1993, now abandoned, which is a continuation of application No. 07/998,645, filed on Dec. 30, 1992, now abandoned, which is a continuation of application No. 07/489,186, filed on Mar. 8, 1990, now abandoned.

(51) Int. Cl.[7] ............................ A61K 38/40; C07K 14/79

(52) U.S. Cl. ................................ 514/8; 514/12; 530/350; 530/395; 530/400

(58) Field of Search .......................... 512/8, 12; 530/350, 530/395, 400

(56) References Cited

U.S. PATENT DOCUMENTS

| | | |
|---|---|---|
| 3,234,199 | 2/1966 | Reid . |
| 3,969,337 | 7/1976 | Laurer et al. . |
| 4,436,658 | 3/1984 | Peyrouset et al. . |
| 4,668,771 | 5/1987 | Kawdkami et al. . |
| 4,732,683 | 3/1988 | Georgidas et al. . |
| 5,571,691 | 11/1996 | Conneely et al. . |
| 5,571,697 | 11/1996 | Conneely et al. . |
| 5,571,896 | 11/1996 | Conneely et al. . |

FOREIGN PATENT DOCUMENTS

| | | |
|---|---|---|
| WO90/13642 | 11/1990 | (WO) . |

OTHER PUBLICATIONS

Maniatis, *Molecular Cloning: A Laboratory Manuel*, Cold Spring Harbor Press, 1989, Chapter 14.

Davis et al., *Basic Methods in Molecular Biology*, Elsevier Science Publishing Co., (1986).

Rado et al., "Isolation of Lactoferrin cDNA from a Human Myeloid Library and Expression of mRNA During Normal and Leukemic Myelopoiesis", *Blood*, 70:4, 989–993, (Oct., 1987).

Tschopp, *Nucleic Acid Research*, vol. 15, p3859–3876, (1987).

Gellisen, "High–Level Expression of Foreign Genes in Hansenula Polymorpha", *Biotech Adv.*, vol. 10, pp. 179–189, 1992.

Gruenwald, *Baculovirus Expression Vector System: Procedures & Methods Manual*, Second Edition, 1993, by Pharmagen.

Rothstein, "One– Step Gene Disruption in Yeast", *Methods in Enzymology*, 101, 202–210, 1983.

Tschopp et al., "High–Level Secretion of Glycosylated Invertase in the Methylotrophic Yeast, *Pichia Pastoris*", *Bio/Technology*, 5, 1305–1308, 1987.

Powell etal., *Nucleic Acid Research*, 18, 4013, 1990.

Bezwoda et al., "Isolation of Characterisation of Lactoferrin Separated from Human whey by Adsorption Chromatography Using Cibacron Blue F3G–A Linked . . . ", *Clin. Chem. Acta.*, 157, 89–94, 1986.

*Chemical Abstracts Service* (CAS) No. 12236–82–7.

Bohme et al., "Affinity Chromatography of Phosphofructokinase Using Cibacron Blue F3G–A", *J. Chromatography*, 69, 209–214, 1972.

Sulkowski, *Frontiers in Bioprocessing*, Sidkar et al., Ed., 343–353, 1990.

Janson et al., *Protein Purification Principle High Resolution Methods and Applications*, VSH Publishers, New York, 1989.

Gubler et al., *Gen*, 40, 1–8, 1983.

Sreekrishna et al., "High–Level Expression, Purification and Characterization of Recombinant Human Tumor Necrosis Factor Synthesized . . . ", *Biochemistry*, 28, 4117–4125, 1989.

Rothstein, *Methods in Enzymology*, 101, 202–210, 1983.

Creeg et al., *Mol. Cell. Biol.*, 5, 3376–3385, 1985.

Hageneson et al., *Enzyme Microb. Technol.*, 11, 650–656, 1989.

Porath et al., *Methods in Enzymology*, 44, 19–45, 1976.

Axen et al., *Nature*, 214, 1302–1304, 1967.

Sanger, *Proc. Nat. Acad. Sci. USA*, 74, 5463–5467, 1977.

Lacemmli, U.K., (1970), *Nature*, 227, 680–685.

Crichton et al., "Iron Transport and Storage", *Eur. J. Biochem.*, vol. 164, 485–506, 1987.

Bezwoda et al., "Lactoferrin from Human Breast Milk and from Neutrophil Granulocytes: Comparative Studies of Isolation, Quantitation", *Biomedical Chromatography*, vol. 3, No. 3, 121–126, 1989.

Sulkowski, "Controlled Pore Glass Chromatography of Proteins", *Protein Purification: Micro to Macro*, 177–195, 1987.

Porath et al., "Thiophilic Interaction and the Selective Adsorption of Proteins", *Tibtech*, vol. 5, 225–229, 1987.

Kaslow, "A Rapid Biochemical Method for Purifying Lambda DNA from Phage Lysstes", *Nucleic Acids Research*, vol. 14, No. 16, 6767, 1986.

(List continued on next page.)

*Primary Examiner*—Gary L. Kunz
*Assistant Examiner*—Stephen Gucker
(74) *Attorney, Agent, or Firm*—Kurt S. Myers

(57) ABSTRACT

Disclosed is human lactoferrin expressed using recombinant DNA, its method of production and purification.

2 Claims, 13 Drawing Sheets

OTHER PUBLICATIONS

Janowicz et al., "Expression System Based on the Methylotrophic Yeast Hansenula Polymorpha", *14th Int. Conf. on Yeast Genetics and Molecular Biology*, S155, E19, John Wiley & Sons, Ltd., 1988.

Pentecost et al., "Lactoferrin Is the Major Estogen Inducible Protein of Mouse Uterine Secretions", *Journal of Biological Chemistry*, vol. 262,No. 21, 10134–10139, 1987.

Wei et al., "Characterization of the Complete cDNA Sequence of Human Neutrophil Lactoferrin and Isolation of Genomic Clones", *Granulocytes and Monocytes*, 155a, No. 530, 1988.

Metz–Boutigue et al., "Human lactoferrin: amino acid sequence and structural comparison with other transferrins", *Eur. J. Biochem.*, 145, 659–676, 1984.

```
    GGATCCGGCCGTAGGAGAAGGAGTGTTCAGTGGTGCGCCGTATCCCAACCCGAGGCCACA
1   ---------+---------+---------+---------+---------+---------+  60
    CCTAGGCCGGCATCCTCTTCCTCACAAGTCACCACGCGGCATAGGGTTGGGCTCCGGTGT
    GlySerGlyArgArgArgArgSerValGlnTrpCysAlaValSerGlnProGluAlaThr

    AAATGCTTCCAATGGCAAAGGAATATGAGAAAAGTGCGTGGCCCTCCTGTCAGCTGCATA
61  ---------+---------+---------+---------+---------+---------+  120
    TTTACGAAGGTTACCGTTTCCTTATACTCTTTTCACGCACCGGGAGGACAGTCGACGTAT
    LysCysPheGlnTrpGlnArgAsnMetArgLysValArgGlyProProValSerCysIle

    AAGAGAGACTCCCCCATCCAGTGTATCCAGGCCATTGCGGAAAACAGGGCCGATGCTGTG
121 ---------+---------+---------+---------+---------+---------+  180
    TTCTCTCTGAGGGGGTAGGTCACATAGGTCCGGTAACGCCTTTTGTCCCGGCTACGACAC
    LysArgAspSerProIleGlnCysIleGlnAlaIleAlaGluAsnArgAlaAspAlaVal

    ACCCTTGATGGTGGTTTCATATACGAGGCAGGCCTGGCCCCCTACAAACTGCGACCTGTA
181 ---------+---------+---------+---------+---------+---------+  240
    TGGGAACTACCACCAAAGTATATGCTCCGTCCGGACCGGGGGATGTTTGACGCTGGACAT
    ThrLeuAspGlyGlyPheIleTyrGluAlaGlyLeuAlaProTyrLysLeuArgProVal

    GCGGCGGAAGTCTACGGGACCGAAAGACAGCCACGAACTCACTATTATGCCGTGGCTGTG
241 ---------+---------+---------+---------+---------+---------+  300
    CGCCGCCTTCAGATGCCCTGGCTTTCTGTCGGTGCTTGAGTGATAATACGGCACCGACAC
    AlaAlaGluValTyrGlyThrGluArgGlnProArgThrHisTyrTyrAlaValAlaVal

    GTGAAGAAGGGCGGCAGcTTTCAGCTGAACGAACTGCAAGGTCTGAAGTCCTGCCACACA
301 ---------+---------+---------+---------+---------+---------+  360
    CACTTCTTCCCGCCGTCgAAAGTCGACTTGCTTGACGTTCCAGACTTCAGGACGGTGTGT
    ValLysLysGlyGlySerPheGlnLeuAsnGluLeuGlnGlyLeuLysSerCysHisThr

    GGCCTTCGCAGGACCGCTGGATGGAATGTCCCTATAGGGACACTTCGTCCATTCTTGAAT
361 ---------+---------+---------+---------+---------+---------+  420
    CCGGAAGCGTCCTGGCGACCTACCTTACAGGGATATCCCTGTGAAGCAGGTAAGAACTTA
    GlyLeuArgArgThrAlaGlyTrpAsnValProIleGlyThrLeuArgProPheLeuAsn

    TGGACGGGTCCACCTGAGCCCATTGAGGCAGCTGTGGCCAGGTTCTTCTCAGCCAGCTGT
421 ---------+---------+---------+---------+---------+---------+  480
    ACCTGCCCAGGTGGACTCGGGTAACTCCGTCGACACCGGTCCAAGAAGAGTCGGTCGACA
    TrpThrGlyProProGluProIleGluAlaAlaValAlaArgPhePheSerAlaSerCys

    GTTCCCGGTGCAGATAAAGGACAGTTCCCCAACCTGTGTCGCCTGTGTGCGGGGACAGGG
481 ---------+---------+---------+---------+---------+---------+  540
    CAAGGGCCACGTCTATTTCCTGTCAAGGGGTTGGACACAGCGGACACACGCCCCTGTCCC
    ValProGlyAlaAspLysGlyGlnPheProAsnLeuCysArgLeuCysAlaGlyThrGly

    GAAAACAAATGTGCCTTCTCCTCCCAGGAACCGTACTTCAGCTACTCTGGTGCCTTCAAG
541 ---------+---------+---------+---------+---------+---------+  600
    CTTTTGTTTACACGGAAGAGGAGGGTCCTTGGCATGAAGTCGATGAGACCACGGAAGTTC
    GluAsnLysCysAlaPheSerSerGlnGluProTyrPheSerTyrSerGlyAlaPheLys
```

FIG. 3a

```
     TGTCTGAGAGACGGGGCTGGAGACGTGGCTTTTATCAGAGAGAGCACAGTGTTTGAGGAC
601  ---------+---------+---------+---------+---------+---------+  660
     ACAGACTCTCTGCCCCGACCTCTGCACCGAAAATAGTCTCTCTCGTGTCACAAACTCCTG
     CysLeuArgAspGlyAlaGlyAspValAlaPheIleArgGluSerThrValPheGluAsp

     CTGTCAGACGAGGCTGAAAGGGACGAGTATGAGTTACTCTGCCCAGACAACACTCGGAAG
661  ---------+---------+---------+---------+---------+---------+  720
     GACAGTCTGCTCCGACTTTCCCTGCTCATACTCAATGAGACGGGTCTGTTGTGAGCCTTC
     LeuSerAspGluAlaGluArgAspGluTyrGluLeuLeuCysProAspAsnThrArgLys

     CCAGTGGACAAGTTCAAAGACTGCCATCTGGCCCGGGTCCCTTCTCATGCCGTTGTGGCA
721  ---------+---------+---------+---------+---------+---------+  780
     GGTCACCTGTTCAAGTTTCTGACGGTAGACCGGGCCCAGGGAAGAGTACGGCAACACCGT
     ProValAspLysPheLysAspCysHisLeuAlaArgValProSerHisAlaValValAla

     CGAAGTGTGAATGGCAAGGAGGATGCCATCTGGAATCTTCTCCGCCAGGCACAGGAAAAG
781  ---------+---------+---------+---------+---------+---------+  840
     GCTTCACACTTACCGTTCCTCCTACGGTAGACCTTAGAAGAGGCGGTCCGTGTCCTTTTC
     ArgSerValAsnGlyLysGluAspAlaIleTrpAsnLeuLeuArgGlnAlaGlnGluLys

     TTTGGAAAGGACAAGTCACCGAAATTCCAGCTCTTTGGCTCCCCTAGTGGGCAGAAAGAT
841  ---------+---------+---------+---------+---------+---------+  900
     AAACCTTTCCTGTTCAGTGGCTTTAAGGTCGAGAAACCGAGGGGATCACCCGTCTTTCTA
     PheGlyLysAspLysSerProLysPheGlnLeuPheGlySerProSerGlyGlnLysAsp

     CTGCTGTTCAAGGACTCTGCCATTGGGTTTTCGAGGGTGCCCCCGAGGATAGATTCTGGG
901  ---------+---------+---------+---------+---------+---------+  960
     GACGACAAGTTCCTGAGACGGTAACCCAAAAGCTCCCACGGGGGCTCCTATCTAAGACCC
     LeuLeuPheLysAspSerAlaIleGlyPheSerArgValProProArgIleAspSerGly

     CTGTACCTTGGCTCCGGCTACTTCACTGCCATCCAGAACTTGAGGAAAAGTGAGGAGGAA
961  ---------+---------+---------+---------+---------+---------+  1020
     GACATGGAACCGAGGCCGATGAAGTGACGGTAGGTCTTGAACTCCTTTTCACTCCTCCTT
     LeuTyrLeuGlySerGlyTyrPheThrAlaIleGlnAsnLeuArgLysSerGluGluGlu

     GTGGCTGCCCGGCGTGCGCGGGTCGTGTGGTGTGCGGTGGGCGAGCAGGAGCTGCGCAAG
1021 ---------+---------+---------+---------+---------+---------+  1080
     CACCGACGGGCCGCACGCGCCCAGCACACCACACGCCACCCGCTCGTCCTCGACGCGTTC
     ValAlaAlaArgArgAlaArgValValTrpCysAlaValGlyGluGlnGluLeuArgLys

     TGTAACCAGTGGAGTGGCTTGAGCGAAGGCAGCGTGACCTGCTCCTCGGCCTCCACCACA
1081 ---------+---------+---------+---------+---------+---------+  1140
     ACATTGGTCACCTCACCGAACTCGCTTCCGTCGCACTGGACGAGGAGCCGGAGGTGGTGT
     CysAsnGlnTrpSerGlyLeuSerGluGlySerValThrCysSerSerAlaSerThrThr

     GAGGACTGCATCGCCCTGGTGCTGAAAGGAGAAGCTGATGCCATGAGTTTGGATGGAGGA
1141 ---------+---------+---------+---------+---------+---------+  1200
     CTCCTGACGTAGCGGGACCACGACTTTCCTCTTCGACTACGGTACTCAAACCTACCTCCT
     GluAspCysIleAlaLeuValLeuLysGlyGluAlaAspAlaMetSerLeuAspGlyGly
```

FIG. 3b

```
     TATGTGTACACTGCAGGCAAATGTGGTTTGGTGCCTGTCCTGGCAGAGAACTACAAATCC
1201 ---------+---------+---------+---------+---------+---------+ 1260
     ATACACATGTGACGTCCGTTTACACCAAACCACGGACAGGACCGTCTCTTGATGTTTAGG
     TyrValTyrThrAlaGlyLysCysGlyLeuValProValLeuAlaGluAsnTyrLysSer

     CAACAAAGCAGTGACCCTGATCCTAACTGTGTGGATAGACCTGTGGAAGGATATCTTGCT
1261 ---------+---------+---------+---------+---------+---------+ 1320
     GTTGTTTCGTCACTGGGACTAGGATTGACACACCTATCTGGACACCTTCCTATAGAACGA
     GlnGlnSerSerAspProAspProAsnCysValAspArgProValGluGlyTyrLeuAla

     GTGGCGGTGGTTAGGAGATCAGACACTAGCCTTACCTGGAACTCTGTGAAAGGCAAGAAG
1321 ---------+---------+---------+---------+---------+---------+ 1380
     CACCGCCACCAATCCTCTAGTCTGTGATCGGAATGGACCTTGAGACACTTTCCGTTCTTC
     ValAlaValValArgArgSerAspThrSerLeuThrTrpAsnSerValLysGlyLysLys

     TCCTGCCACACCGCCGTGGACAGGACTGCAGGCTGGAATATCCCCATGGGCCTGCTCTTC
1381 ---------+---------+---------+---------+---------+---------+ 1440
     AGGACGGTGTGGCGGCACCTGTCCTGACGTCCGACCTTATAGGGGTACCCGGACGAGAAG
     SerCysHisThrAlaValAspArgThrAlaGlyTrpAsnIleProMetGlyLeuLeuPhe

     AACCAGACGGGCTCCTGCAAATTTGATGAATATTTCAGTCAAAGCTGTGCCCCTGGGTCT
1441 ---------+---------+---------+---------+---------+---------+ 1500
     TTGGTCTGCCCGAGGACGTTTAAACTACTTATAAAGTCAGTTTCGACACGGGGACCCAGA
     AsnGlnThrGlySerCysLysPheAspGluTyrPheSerGlnSerCysAlaProGlySer

     GACCCGAGATCTAAtCTCTGTGCTCTGTGTATTGGCGACGAGCAGGGTGAGAATAAGTGC
1501 ---------+---------+---------+---------+---------+---------+ 1560
     CTGGGCTCTAGATTaGAGACACGAGACACATAACCGCTGCTCGTCCCACTCTTATTCACG
     AspProArgSerAsnLeuCysAlaLeuCysIleGlyAspGluGlnGlyGluAsnLysCys

     GTGCCCAACAGCAACGAGAGATACTACGGCTACACTGGGGCTTTCCGGTGCCTGGCTGAG
1561 ---------+---------+---------+---------+---------+---------+ 1620
     CACGGGTTGTCGTTGCTCTCTATGATGCCGATGTGACCCCGAAAGGCCACGGACCGACTC
     ValProAsnSerAsnGluArgTyrTyrGlyTyrThrGlyAlaPheArgCysLeuAlaGlu

     AATGCTGGAGACGTTGCATTTGTGAAAGATGTCACTGTCTTGCAGAACACTGATGGAAAT
1621 ---------+---------+---------+---------+---------+---------+ 1680
     TTACGACCTCTGCAACGTAAACACTTTCTACAGTGACAGAACGTCTTGTGACTACCTTTA
     AsnAlaGlyAspValAlaPheValLysAspValThrValLeuGlnAsnThrAspGlyAsn

     AACAATGAGGCATGGGCTAAGGATTTGAAGCTGGCAGACTTTGCGCTGCTGTGCCTCGAT
1681 ---------+---------+---------+---------+---------+---------+ 1740
     TTGTTACTCCGTACCCGATTCCTAAACTTCGACCGTCTGAAACGCGACGACACGGAGCTA
     AsnAsnGluAlaTrpAlaLysAspLeuLysLeuAlaAspPheAlaLeuLeuCysLeuAsp

     GGCAAACGGAAGCCTGTGACTGAGGCTAGAAGCTGCCATCTTGCCATGGCCCCGAATCAT
1741 ---------+---------+---------+---------+---------+---------+ 1800
     CCGTTTGCCTTCGGACACTGACTCCGATCTTCGACGGTAGAACGGTACCGGGGCTTAGTA
     GlyLysArgLysProValThrGluAlaArgSerCysHisLeuAlaMetAlaProAsnHis
```

FIG. 3c

```
       GCCGTGGTGTCTCGGATGGATAAGGTGGAACGCCTGAAACAGGTGTTGCTCCACCAACAG
1801   ---------+---------+---------+---------+---------+---------+   1860
       CGGCACCACAGAGCCTACCTATTCCACCTTGCGGACTTTGTCCACAACGAGGTGGTTGTC
       AlaValValSerArgMetAspLysValGluArgLeuLysGlnValLeuLeuHisGlnGln

       GCTAAATTTGGGAGAAATGGATCTGACTGCCCGGACAAGTTTTGCTTATTCCAGTCTGAA
1861   ---------+---------+---------+---------+---------+---------+   1920
       CGATTTAAACCCTCTTTACCTAGACTGACGGGCCTGTTCAAAACGAATAAGGTCAGACTT
       AlaLysPheGlyArgAsnGlySerAspCysProAspLysPheCysLeuPheGlnSerGlu

       ACCAAAAACCTTCTGTTCAATGACAACACTGAGTGTCTGGCCAGACTCCATGGCAAAACA
1921   ---------+---------+---------+---------+---------+---------+   1980
       TGGTTTTTGGAAGACAAGTTACTGTTGTGACTCACAGACCGGTCTGAGGTACCGTTTTGT
       ThrLysAsnLeuLeuPheAsnAspAsnThrGluCysLeuAlaArgLeuHisGlyLysThr

       ACATATGAAAAATATTTGGGACCACAGTATGTCGCAGGCATTACTAATCTGAAAAAGTGC
1981   ---------+---------+---------+---------+---------+---------+   2040
       TGTATACTTTTTATAAACCCTGGTGTCATACAGCGTCCGTAATGATTAGACTTTTTCACG
       ThrTyrGluLysTyrLeuGlyProGlnTyrValAlaGlyIleThrAsnLeuLysLysCys

       TCAACCTCCCCCCTCCTGGAAGCCTGTGAATTCCTCAGGAAGTAAA
2041   ---------+---------+---------+---------+------   2086
       AGTTGGAGGGGGGAGGACCTTCGGACACTTAAGGAGTCCTTCATTT
       SerThrSerProLeuLeuGluAlaCysGluPheLeuArgLysEnd
```

FIG. 3d

BgLI 1 404 820 1795 2109

HgIAI 1 691 1571 2109

Pvu II 1 163 509 524 2109

Stu I 1 266 411 2109

```
                              SEQUENCE LISTING

(1) GENERAL INFORMATION:

   (iii) NUMBER OF SEQUENCES: 8

(2) INFORMATION FOR SEQ ID NO:1:

     (i) SEQUENCE CHARACTERISTICS:
          (A) LENGTH: 2086 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (ix) FEATURE:
          (A) NAME/KEY: CDS
          (B) LOCATION: 1..2086

    (xi) SEQUENCE DESCRIPTION: SEQ ID NO:1:

GGA TCC GGC CGT AGG AGA AGG AGT GTT CAG TGG TGC GCC GTA TCC CAA       48
Gly Ser Gly Arg Arg Arg Arg Ser Val Gln Trp Cys Ala Val Ser Gln
  1               5                  10                  15

CCC GAG GCC ACA AAA TGC TTC CAA TGG CAA AGG AAT ATG AGA AAA GTG       96
Pro Glu Ala Thr Lys Cys Phe Gln Trp Gln Arg Asn Met Arg Lys Val
             20                  25                  30

CGT GGC CCT CCT GTC AGC TGC ATA AAG AGA GAC TCC CCC ATC CAG TGT      144
Arg Gly Pro Pro Val Ser Cys Ile Lys Arg Asp Ser Pro Ile Gln Cys
         35                  40                  45

ATC CAG GCC ATT GCG GAA AAC AGG GCC GAT GCT GTG ACC CTT GAT GGT      192
Ile Gln Ala Ile Ala Glu Asn Arg Ala Asp Ala Val Thr Leu Asp Gly
     50                  55                  60

GGT TTC ATA TAC GAG GCA GGC CTG GCC CCC TAC AAA CTG CGA CCT GTA      240
Gly Phe Ile Tyr Glu Ala Gly Leu Ala Pro Tyr Lys Leu Arg Pro Val
 65                  70                  75                  80

GCG GCG GAA GTC TAC GGG ACC GAA AGA CAG CCA CGA ACT CAC TAT TAT      288
Ala Ala Glu Val Tyr Gly Thr Glu Arg Gln Pro Arg Thr His Tyr Tyr
                 85                  90                  95

GCC GTG GCT GTG GTG AAG AAG GGC GGC AGC TTT CAG CTG AAC GAA CTG      336
Ala Val Ala Val Val Lys Lys Gly Gly Ser Phe Gln Leu Asn Glu Leu
            100                 105                 110

CAA GGT CTG AAG TCC TGC CAC ACA GGC CTT CGC AGG ACC GCT GGA TGG      384
Gln Gly Leu Lys Ser Cys His Thr Gly Leu Arg Arg Thr Ala Gly Trp
        115                 120                 125
```

-continued

```
AAT GTC CCT ATA GGG ACA CTT CGT CCA TTC TTG AAT TGG ACG GGT CCA      432
Asn Val Pro Ile Gly Thr Leu Arg Pro Phe Leu Asn Trp Thr Gly Pro
    130                 135                 140

CCT GAG CCC ATT GAG GCA GCT GTG GCC AGG TTC TTC TCA GCC AGC TGT      480
Pro Glu Pro Ile Glu Ala Ala Val Ala Arg Phe Phe Ser Ala Ser Cys
145                 150                 155                 160

GTT CCC GGT GCA GAT AAA GGA CAG TTC CCC AAC CTG TGT CGC CTG TGT      528
Val Pro Gly Ala Asp Lys Gly Gln Phe Pro Asn Leu Cys Arg Leu Cys
                165                 170                 175

GCG GGG ACA GGG GAA AAC AAA TGT GCC TTC TCC TCC CAG GAA CCG TAC      576
Ala Gly Thr Gly Glu Asn Lys Cys Ala Phe Ser Ser Gln Glu Pro Tyr
            180                 185                 190

TTC AGC TAC TCT GGT GCC TTC AAG TGT CTG AGA GAC GGG GCT GGA GAC      624
Phe Ser Tyr Ser Gly Ala Phe Lys Cys Leu Arg Asp Gly Ala Gly Asp
        195                 200                 205

GTG GCT TTT ATC AGA GAG AGC ACA GTG TTT GAG GAC CTG TCA GAC GAG      672
Val Ala Phe Ile Arg Glu Ser Thr Val Phe Glu Asp Leu Ser Asp Glu
    210                 215                 220

GCT GAA AGG GAC GAG TAT GAG TTA CTC TGC CCA GAC AAC ACT CGG AAG      720
Ala Glu Arg Asp Glu Tyr Glu Leu Leu Cys Pro Asp Asn Thr Arg Lys
225                 230                 235                 240

CCA GTG GAC AAG TTC AAA GAC TGC CAT CTG GCC CGG GTC CCT TCT CAT      768
Pro Val Asp Lys Phe Lys Asp Cys His Leu Ala Arg Val Pro Ser His
                245                 250                 255

GCC GTT GTG GCA CGA AGT GTG AAT GGC AAG GAG GAT GCC ATC TGG AAT      816
Ala Val Val Ala Arg Ser Val Asn Gly Lys Glu Asp Ala Ile Trp Asn
            260                 265                 270

CTT CTC CGC CAG GCA CAG GAA AAG TTT GGA AAG GAC AAG TCA CCG AAA      864
Leu Leu Arg Gln Ala Gln Glu Lys Phe Gly Lys Asp Lys Ser Pro Lys
        275                 280                 285

TTC CAG CTC TTT GGC TCC CCT AGT GGG CAG AAA GAT CTG CTG TTC AAG      912
Phe Gln Leu Phe Gly Ser Pro Ser Gly Gln Lys Asp Leu Leu Phe Lys
    290                 295                 300

GAC TCT GCC ATT GGG TTT TCG AGG GTG CCC CCG AGG ATA GAT TCT GGG      960
Asp Ser Ala Ile Gly Phe Ser Arg Val Pro Pro Arg Ile Asp Ser Gly
305                 310                 315                 320

CTG TAC CTT GGC TCC GGC TAC TTC ACT GCC ATC CAG AAC TTG AGG AAA     1008
Leu Tyr Leu Gly Ser Gly Tyr Phe Thr Ala Ile Gln Asn Leu Arg Lys
                325                 330                 335

AGT GAG GAG GAA GTG GCT GCC CGG CGT GCG CGG GTC GTG TGG TGT GCG     1056
Ser Glu Glu Glu Val Ala Ala Arg Arg Ala Arg Val Val Trp Cys Ala
            340                 345                 350

GTG GGC GAG CAG GAG CTG CGC AAG TGT AAC CAG TGG AGT GGC TTG AGC     1104
Val Gly Glu Gln Glu Leu Arg Lys Cys Asn Gln Trp Ser Gly Leu Ser
        355                 360                 365

GAA GGC AGC GTG ACC TGC TCC TCG GCC TCC ACC ACA GAG GAC TGC ATC     1152
Glu Gly Ser Val Thr Cys Ser Ser Ala Ser Thr Thr Glu Asp Cys Ile
    370                 375                 380

GCC CTG GTG CTG AAA GGA GAA GCT GAT GCC ATG AGT TTG GAT GGA GGA     1200
Ala Leu Val Leu Lys Gly Glu Ala Asp Ala Met Ser Leu Asp Gly Gly
385                 390                 395                 400

TAT GTG TAC ACT GCA GGC AAA TGT GGT TTG GTG CCT GTC CTG GCA GAG     1248
Tyr Val Tyr Thr Ala Gly Lys Cys Gly Leu Val Pro Val Leu Ala Glu
                405                 410                 415

AAC TAC AAA TCC CAA CAA AGC AGT GAC CCT GAT CCT AAC TGT GTG GAT     1296
Asn Tyr Lys Ser Gln Gln Ser Ser Asp Pro Asp Pro Asn Cys Val Asp
            420                 425                 430

AGA CCT GTG GAA GGA TAT CTT GCT GTG GCG GTG GTT AGG AGA TCA GAC     1344
Arg Pro Val Glu Gly Tyr Leu Ala Val Ala Val Val Arg Arg Ser Asp
```

-continued

```
        435                 440                 445

ACT AGC CTT ACC TGG AAC TCT GTG AAA GGC AAG AAG TCC TGC CAC ACC      1392
Thr Ser Leu Thr Trp Asn Ser Val Lys Gly Lys Lys Ser Cys His Thr
    450                 455                 460

GCC GTG GAC AGG ACT GCA GGC TGG AAT ATC CCC ATG GGC CTG CTC TTC      1440
Ala Val Asp Arg Thr Ala Gly Trp Asn Ile Pro Met Gly Leu Leu Phe
465                 470                 475                 480

AAC CAG ACG GGC TCC TGC AAA TTT GAT GAA TAT TTC AGT CAA AGC TGT      1488
Asn Gln Thr Gly Ser Cys Lys Phe Asp Glu Tyr Phe Ser Gln Ser Cys
                485                 490                 495

GCC CCT GGG TCT GAC CCG AGA TCT AAT CTC TGT GCT CTG TGT ATT GGC      1536
Ala Pro Gly Ser Asp Pro Arg Ser Asn Leu Cys Ala Leu Cys Ile Gly
            500                 505                 510

GAC GAG CAG GGT GAG AAT AAG TGC GTG CCC AAC AGC AAC GAG AGA TAC      1584
Asp Glu Gln Gly Glu Asn Lys Cys Val Pro Asn Ser Asn Glu Arg Tyr
        515                 520                 525

TAC GGC TAC ACT GGG GCT TTC CGG TGC CTG GCT GAG AAT GCT GGA GAC      1632
Tyr Gly Tyr Thr Gly Ala Phe Arg Cys Leu Ala Glu Asn Ala Gly Asp
    530                 535                 540

GTT GCA TTT GTG AAA GAT GTC ACT GTC TTG CAG AAC ACT GAT GGA AAT      1680
Val Ala Phe Val Lys Asp Val Thr Val Leu Gln Asn Thr Asp Gly Asn
545                 550                 555                 560

AAC AAT GAG GCA TGG GCT AAG GAT TTG AAG CTG GCA GAC TTT GCG CTG      1728
Asn Asn Glu Ala Trp Ala Lys Asp Leu Lys Leu Ala Asp Phe Ala Leu
                565                 570                 575

CTG TGC CTC GAT GGC AAA CGG AAG CCT GTG ACT GAG GCT AGA AGC TGC      1776
Leu Cys Leu Asp Gly Lys Arg Lys Pro Val Thr Glu Ala Arg Ser Cys
            580                 585                 590

CAT CTT GCC ATG GCC CCG AAT CAT GCC GTG GTG TCT CGG ATG GAT AAG      1824
His Leu Ala Met Ala Pro Asn His Ala Val Val Ser Arg Met Asp Lys
        595                 600                 605

GTG GAA CGC CTG AAA CAG GTG TTG CTC CAC CAA CAG GCT AAA TTT GGG      1872
Val Glu Arg Leu Lys Gln Val Leu Leu His Gln Gln Ala Lys Phe Gly
    610                 615                 620

AGA AAT GGA TCT GAC TGC CCG GAC AAG TTT TGC TTA TTC CAG TCT GAA      1920
Arg Asn Gly Ser Asp Cys Pro Asp Lys Phe Cys Leu Phe Gln Ser Glu
625                 630                 635                 640

ACC AAA AAC CTT CTG TTC AAT GAC AAC ACT GAG TGT CTG GCC AGA CTC      1968
Thr Lys Asn Leu Leu Phe Asn Asp Asn Thr Glu Cys Leu Ala Arg Leu
                645                 650                 655

CAT GGC AAA ACA ACA TAT GAA AAA TAT TTG GGA CCA CAG TAT GTC GCA      2016
His Gly Lys Thr Thr Tyr Glu Lys Tyr Leu Gly Pro Gln Tyr Val Ala
            660                 665                 670

GGC ATT ACT AAT CTG AAA AAG TGC TCA ACC TCC CCC CTC CTG GAA GCC      2064
Gly Ile Thr Asn Leu Lys Lys Cys Ser Thr Ser Pro Leu Leu Glu Ala
        675                 680                 685

TGT GAA TTC CTC AGG AAG TAA A                                        2086
Cys Glu Phe Leu Arg Lys  *
    690                 695
```

(2) INFORMATION FOR SEQ ID NO:2:

(i) SEQUENCE CHARACTERISTICS:
(A) LENGTH: 694 amino acids
(B) TYPE: amino acid
(D) TOPOLOGY: linear (ii) MOLECULE TYPE: protein (xi) SEQUENCE DESCRIPTION: SEQ ID NO:2:

```
Gly Ser Gly Arg Arg Arg Arg Ser Val Gln Trp Cys Ala Val Ser Gln
```

-continued

```
 1               5                  10                  15

Pro Glu Ala Thr Lys Cys Phe Gln Trp Gln Arg Asn Met Arg Lys Val
             20                  25                  30

Arg Gly Pro Pro Val Ser Cys Ile Lys Arg Asp Ser Pro Ile Gln Cys
         35                  40                  45

Ile Gln Ala Ile Ala Glu Asn Arg Ala Asp Ala Val Thr Leu Asp Gly
     50                  55                  60

Gly Phe Ile Tyr Glu Ala Gly Leu Ala Pro Tyr Lys Leu Arg Pro Val
 65                  70                  75                  80

Ala Ala Glu Val Tyr Gly Thr Glu Arg Gln Pro Arg Thr His Tyr Tyr
                 85                  90                  95

Ala Val Ala Val Val Lys Lys Gly Gly Ser Phe Gln Leu Asn Glu Leu
            100                 105                 110

Gln Gly Leu Lys Ser Cys His Thr Gly Leu Arg Arg Thr Ala Gly Trp
        115                 120                 125

Asn Val Pro Ile Gly Thr Leu Arg Pro Phe Leu Asn Trp Thr Gly Pro
    130                 135                 140

Pro Glu Pro Ile Glu Ala Ala Val Ala Arg Phe Phe Ser Ala Ser Cys
145                 150                 155                 160

Val Pro Gly Ala Asp Lys Gly Gln Phe Pro Asn Leu Cys Arg Leu Cys
                165                 170                 175

Ala Gly Thr Gly Glu Asn Lys Cys Ala Phe Ser Ser Gln Glu Pro Tyr
            180                 185                 190

Phe Ser Tyr Ser Gly Ala Phe Lys Cys Leu Arg Asp Gly Ala Gly Asp
        195                 200                 205

Val Ala Phe Ile Arg Glu Ser Thr Val Phe Glu Asp Leu Ser Asp Glu
    210                 215                 220

Ala Glu Arg Asp Glu Tyr Glu Leu Leu Cys Pro Asp Asn Thr Arg Lys
225                 230                 235                 240

Pro Val Asp Lys Phe Lys Asp Cys His Leu Ala Arg Val Pro Ser His
                245                 250                 255

Ala Val Val Ala Arg Ser Val Asn Gly Lys Glu Asp Ala Ile Trp Asn
            260                 265                 270

Leu Leu Arg Gln Ala Gln Glu Lys Phe Gly Lys Asp Lys Ser Pro Lys
        275                 280                 285

Phe Gln Leu Phe Gly Ser Pro Ser Gly Gln Lys Asp Leu Leu Phe Lys
    290                 295                 300

Asp Ser Ala Ile Gly Phe Ser Arg Val Pro Pro Arg Ile Asp Ser Gly
305                 310                 315                 320

Leu Tyr Leu Gly Ser Gly Tyr Phe Thr Ala Ile Gln Asn Leu Arg Lys
                325                 330                 335

Ser Glu Glu Glu Val Ala Ala Arg Arg Ala Arg Val Val Trp Cys Ala
            340                 345                 350

Val Gly Glu Gln Glu Leu Arg Lys Cys Asn Gln Trp Ser Gly Leu Ser
        355                 360                 365

Glu Gly Ser Val Thr Cys Ser Ser Ala Ser Thr Thr Glu Asp Cys Ile
    370                 375                 380

Ala Leu Val Leu Lys Gly Glu Ala Asp Ala Met Ser Leu Asp Gly Gly
385                 390                 395                 400

Tyr Val Tyr Thr Ala Gly Lys Cys Gly Leu Val Pro Val Leu Ala Glu
                405                 410                 415

Asn Tyr Lys Ser Gln Gln Ser Ser Asp Pro Asp Pro Asn Cys Val Asp
            420                 425                 430
```

-continued

```
Arg Pro Val Glu Gly Tyr Leu Ala Val Ala Val Val Arg Arg Ser Asp
        435                 440                 445

Thr Ser Leu Thr Trp Asn Ser Val Lys Gly Lys Lys Ser Cys His Thr
    450                 455                 460

Ala Val Asp Arg Thr Ala Gly Trp Asn Ile Pro Met Gly Leu Leu Phe
465                 470                 475                 480

Asn Gln Thr Gly Ser Cys Lys Phe Asp Glu Tyr Phe Ser Gln Ser Cys
                485                 490                 495

Ala Pro Gly Ser Asp Pro Arg Ser Asn Leu Cys Ala Leu Cys Ile Gly
            500                 505                 510

Asp Glu Gln Gly Glu Asn Lys Cys Val Pro Asn Ser Asn Glu Arg Tyr
        515                 520                 525

Tyr Gly Tyr Thr Gly Ala Phe Arg Cys Leu Ala Glu Asn Ala Gly Asp
    530                 535                 540

Val Ala Phe Val Lys Asp Val Thr Val Leu Gln Asn Thr Asp Gly Asn
545                 550                 555                 560

Asn Asn Glu Ala Trp Ala Lys Asp Leu Lys Leu Ala Asp Phe Ala Leu
                565                 570                 575

Leu Cys Leu Asp Gly Lys Arg Lys Pro Val Thr Glu Ala Arg Ser Cys
            580                 585                 590

His Leu Ala Met Ala Pro Asn His Ala Val Val Ser Arg Met Asp Lys
        595                 600                 605

Val Glu Arg Leu Lys Gln Val Leu Leu His Gln Gln Ala Lys Phe Gly
    610                 615                 620

Arg Asn Gly Ser Asp Cys Pro Asp Lys Phe Cys Leu Phe Gln Ser Glu
625                 630                 635                 640

Thr Lys Asn Leu Leu Phe Asn Asp Asn Thr Glu Cys Leu Ala Arg Leu
                645                 650                 655

His Gly Lys Thr Thr Tyr Glu Lys Tyr Leu Gly Pro Gln Tyr Val Ala
            660                 665                 670

Gly Ile Thr Asn Leu Lys Lys Cys Ser Thr Ser Pro Leu Leu Glu Ala
        675                 680                 685

Cys Glu Phe Leu Arg Lys
    690                 695
```

```
(2) INFORMATION FOR SEQ ID NO:3:

     (i) SEQUENCE CHARACTERISTICS:
          (A) LENGTH:  35 amino acids
          (B) TYPE: nucleic acid
          (C) STRANDEDNESS: single
          (D) TOPOLOGY: linear

    (ii) MOLECULE TYPE: protein

   (iii) HYPOTHETICAL: NO

    (iv) ANTI-SENSE: NO

    (xi) SEQUENCE DESCRIPTION: SEQ ID NO:3:

AGCGGATCCG GCCGTAGGAG AAGGAGTGTT CAGTGG                              36


(2) INFORMATION FOR SEQ ID NO:4:

     (i) SEQUENCE CHARACTERISTICS:
          (A) LENGTH:  32 amino acids
          (B) TYPE: nucleic acid
          (C) STRANDEDNESS: single
          (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO:4:

CGATCTAGAT TACTTCCTGA GGAATCCACA GGC 33

(2) INFORMATION FOR SEQ ID NO:5:

(i) SEQUENCE CHARACTERISTICS:
(A) LENGTH: 41 amino acids
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

AAGCTTATGA AACTTGTCTT CCTCGTCCTG TTCTTCCTCG GG 42

(2) INFORMATION FOR SEQ ID NO:6:

(i) SEQUENCE CHARACTERISTICS:
(A) LENGTH: 34 amino acids
(B) TYPE: nucleic acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:6:

GATCCAGCCA GAGAGAGTCC GAGGGCCCCG AGGAA 35

(2) INFORMATION FOR SEQ ID NO:7:

(i) SEQUENCE CHARACTERISTICS:
(A) LENGTH: 27 amino acids
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

ATTATTCGAA ACGAGGAATT AGCTTATG 28

(2) INFORMATION FOR SEQ ID NO:8:

(i) SEQUENCE CHARACTERISTICS:
(A) LENGTH: 21 amino acids
(B) TYPE: nucleic acid
(C) STRANDEDNESS: single
(D) TOPOLOGY: linear (ii) MOLECULE TYPE: DNA (genomic)

-continued

```
   (iii) HYPOTHETICAL: NO

    (iv) ANTI-SENSE: NO

    (xi) SEQUENCE DESCRIPTION: SEQ ID NO:8:

TCGAGAAAAG ACTTTTCTCC GG                                              22
```

HUMAN LACTOFERRIN

RELATED APPLICATIONS

This application is a division of application Ser. No. 08/724,586, filed Sep. 30, 1996 now U.S. Pat. No. 6,066, 469, which is a continuation of application Ser. No. 08/238, 445, filed May 5, 1994 now abandoned, which is a continuation-in-part of application Ser. No. 08/132,218, filed Oct. 6, 1993 now abandoned, which is a continuation of application Ser. No. 07/998,645, filed Dec. 30, 1992 (now abandoned), which is a continuation of application Ser. No. 07/489,186, filed Mar. 8, 1990 (now abandoned), the disclosure of which are incorporated herein by reference.

FIELD OF THE INVENTION

The present invention relates generally to the glycoprotein lactoferrin, its production, purification, and uses.

BACKGROUND OF THE INVENTION

Lactoferrin plays an important role in iron transport and utilization in humans. A glycoprotein containing about 6% sugar and having a total molecular weight of about 80,000 daltons, human lactoferrin is capable of binding two ferric ions with high affinity. Although lactoferrin binds iron tightly, the binding is reversible so that the metal is available upon demand to cells with a need for this essential element. The metal is captured by the side chains of specific amino acids: two tyrosines, one histidine and one aspartate which in combination form a cleft in the surface of the protein. That portion of the protein which contains the aforesaid four amino acids and forms the cleft is termed the "iron-binding domain." Each natural lactofeltin molecule has two iron-binding domains.

Human milk is high in lactoferrin content. The high degree of iron absorption from human milk is manifested in a low incidence of iron deficiency anemia among breast fed infants compared to infants fed with cow's milk. Accordingly, lactoferrin is a key protein for healthy development of infants. Lactoferrin also plays an important role in cell-mediated host immunity. It is present in high concentrations in all bodily secretions, such as tears, sweat, and ciliated respiratory mucous. Because it sequesters iron, lactoferrin can neutralize pathogenic microorganisms by preventing them from obtaining necessary iron at the site of entry, thereby preventing the spread of infection.

Although iron is an essential material in humans, excess iron in the body can induce pathological conditions as well. Chronic iron overload, known as hemosiderosis, is characterized by a greater than normal local or generalized deposition of iron within certain body tissues. Lactoferrin helps to manage the balance of free iron in the body to prevent occurrence of such pathological states in healthy individuals.

The severely limited amount of human milk, the major source of human lactoferrin, restricts lactoferrin production. Furthermore, production of lactoferrin from human milk presents a risk factor of infectious contamination. That is, it could carry with it a potentially lethal contaminant, such as the human immunodeficiency virus (HIV) or another undesirable agent.

SUMMARY OF THE INVENTION

Accordingly, the present invention provides for the cloning and expression of human lactoferrin using recombinant DNA techniques. The lactoferrin of the present invention is free of naturally occurring contaminants, e.g., proteins and viruses, that would be detrimental to the recipient.

In one embodiment of the present invention there is provided a gene comprising a DNA molecule encoding human lactoferrin protein. More particularly, the DNA molecule comprises the nucleotide sequence (Seq. ID No. 1) and the protein comprises the amino acid sequence (Seq. ID No. 2) as substantially depicted in FIG. 3. An expression system is provided for expressing the gene encoding the protein. Preferably, the expression system is a plasmid. Also described herein, is a host cell line transformed with the gene of the present invention, i.e., the gene encoding human lactoferrin. Preferably the host cell organism is a eukaryotic cell.

In another embodiment of the invention, there is provided a method of producing human lactoferrin comprising the steps of (a) isolating a gene encoding human lactoferrin; (b) transforming a host cell with the gene; (c) culturing the transformed cells which express the gene product; and (d) collecting lactoferrin from the cells.

In a further embodiment of the invention there is described a cluomatography method for purifying lactoferrin protein, and other proteins, comprising the steps of (a) contacting a substance with a first adsorbent to obtain adsorbed and non-absorbed fractions; (b) eluting the adsorbed fraction with an eluant; and (c) contacting the adsorbed fraction with a second adsorbent, wherein the improvement comprises equilibrating the second adsorbent with the eluant followed by contacting the eluate containing the adsorbed fraction with the second adsorbent.

In still a further embodiment of the invention there is provided a method for inhibiting microbial growth in a mammal comprising topically or systemically applying to a subject a therapeutically effective amount of lactoferrin having less than about 25% metal loading; a method for inhibiting iron deficiency in a manual comprising orally administering a therapeutically effective amount of lactoferrin having at least about 35% iron loading; a nutritional supplement comprising an iron-loaded human lactoferrin having at least about 35% metal loading and a nutritionally acceptable carrier or adjuvant; a topical antiseptic comprising a therapeutically effective amount of lactoferrin having less than about 25% metal loading and a pharmaceutically acceptable carrier or diluent; and a method for inhibiting food spoilage comprising adding to the food an effective amount of lactoferrin having less than about 25% metal loading.

BRIEF DESCRIPTION OF THE DRAWINGS

FIGS. 3*a*–3*d* show the nucleotide sequence (Seq. ID No. 1) and the deduced amino acid sequence (Seq. ID No. 2) of the gene encoding human lactoferrin.

FIG. 10 is a Western blot analysis of the recombinantly expressed lactoferrin according to the present invention.

BRIEF DESCRIPTION OF THE INVENTION

Figure 1:
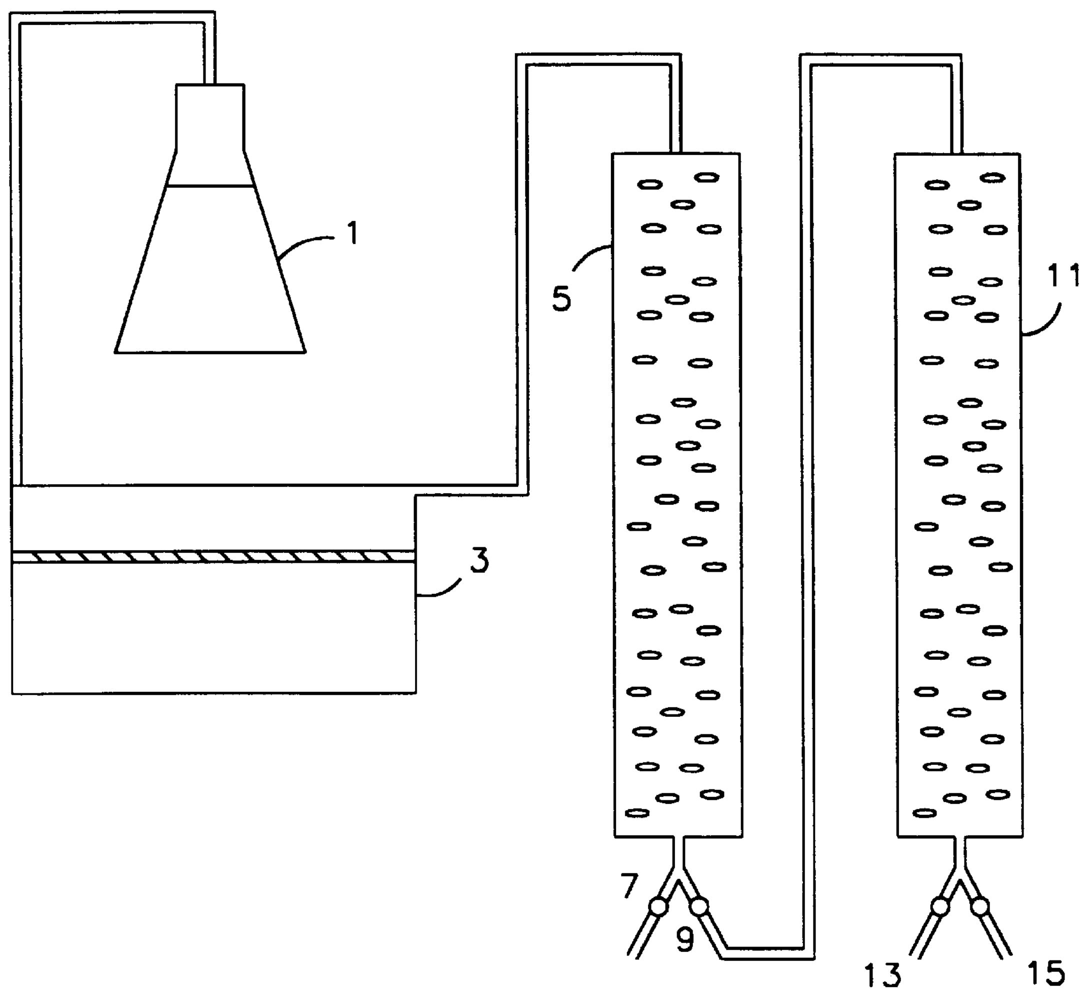
FIG. 1 is a schematic diagram showing the chromatography method of the invention.

Lactoferrin is produced in accordance with the present invention using recombinant DNA technology to produce genetically modified DNA that expresses lactoferrin. The recombinant DNA technology described herein is standard technology in the art, such as described by Maniatis, *Molecular Cloning: A Laboratory Manual*, Cold Spring Harbor Press, 1989, Chapter 14, which disclosure is hereby incorporated by reference. That is, a polypeptide containing the primary structural conformation of the naturally occurring human lactoferrin protein, having similar biological (i.e. physical) properties is produced. The DNA encoding lactoferrin is preferably from a cDNA library derived from human RNA and ligated to an appropriate expression vector according to standard techniques in the art, such as those disclosed in Davis, et al., *Basic Methods in Molecular Biology*, Elsevier Science Publishing Co. (1986), which disclosure is hereby incorporated by reference. Preferably, the RNA is isolated from the human mammary gland and the preferred vector is phage λgt11. The cDNA library is screened for positive (DNA carrying the lactoferrin gene) clones using conventional techniques in the art, such as disclosed by Davis, et al., supra, and Rado, et al., *Blood*, 70:4, 989–993 (October, 1987), which disclosure is hereby incorporated by reference. For example, the cDNA is hybridized to a radiolabeled oligonucleotide probe and the positive clones identified by auto radiography. Preferably, positive clones are identified using lactoferrin antisera, and an appropriate development system, such as an avidin/biotin reaction system. Large numbers of positive clones are then generated by infecting an appropriate bacterial host, such as *E. coli* Y 1090, using methods that will be readily apparent to the skilled artisan such as described by Davis, et al. (1986), supra. DNA is then isolated from the clones. The cDNA encoding lactoferrin is thereafter cut with an appropriate restriction endonuclease such as EcoRI. The cut DNA encoding lactoferrin is separated by chromatography. Preferably, the separated cDNA is further sub-cloned into another vector, such as the pGEM-4 plasmid, and the inserted cDNA again excised and separated.

Expression of human lactoferrin according to the present invention is performed using an appropriate host organism, such as the yeast *Pichia pastoris* with an appropriate expression vector such as those driven by the alcohol oxidase promoter and disclosed in Tschopp, *Nucleic Acid Research*, Vol. 15, pp. 3859–3876, (1987). Other useful hosts include: (i) the yeast *Hansenula polymorpha* with an appropriate expression vector driven by strong promoters such as methanol oxidase (MOX), dihydroxyacetone synthetase (DAS), or formate dehydrogenase (FMDH) as disclosed in Gellisen, *Biotech. Adv.*, Vol 10, pp. 179–189, (1992) the disclosure of which is incorporated herewith by reference; and (ii) the *Spodoptera frugiperda* insect cells with an appropriate expression vector such as a Baculovirus expression vector system driven by polyhedrin promoter as disclosed in Gruenwald, *Baculovirus Expression Vector System: Procedures & Methods Manual*, Second Edition, 1993 by Pharmingen, the disclosure of which is incorporated by reference herein.

Insertion of the cDNA and expression of the human lactoferrin are carried out using standard recombinant techniques that are readily apparent to one skilled in the art, such as described in Rothstein, *Methods in Enzymology*, 101, 202–210 (1983); and Tschopp, et al., *Bio/Technology*, 5, 1305–1308 (1987), which disclosures are hereby incorporated by reference.

In a preferred embodiment, to obtain the full length cDNA clone of lactoferrin, the gene is amplified from a human mammary gland library using the polymerase chain reaction (PCR) technique. Preferably, amplification of the insert encoding the lactoferrin gene is achieved by using two synthetic oligonucleotide probes corresponding to the amino acid sequence residues 1 to 9 of the amino terminus and residues 2070 to 2079 of the carboxy terminus. The amplified insert is cut out with restriction enzymes BamH I and Xba I, then purified, and ligated into an appropriate vector, preferably pBlueScriptKS+, which is digested with the same restriction enzymes. The lactoferrin gene is further subcloned into pUC118 vector, cut with Hind III and Sst I to produce a plasmid designated pUC118-LF, containing the coding region for the mature lactoferrin protein. Secretion of the lactoferrin protein may be further enhanced by further manipulations of plasmid pUC118-LF. For example, the following two methods are provided for purposes of illustration.

The first method is the addition of a signal sequence to the 5' end of the clone. The preferred signal sequence is that described by Powell, et al., *Nucleic Acids Research*, 18, 4013 (1990), which disclosure is hereby incorporated by reference. pUC118-LF modified with the aforementioned signal sequence is defined as pUC118-LFS. Preferably, the lactoferrin gene, together with the signal sequence is cut from pUC118-LFS and then ligated to pHIL-D1 to produce pHIL-D1-LFS.

The second, and more preferable, method employs the alpha mating factor pre-pro secretion signal. The mature lactoferrin gene is cut from plasmid pUC118-LF and ligated to plasmid pPIC9 which had been previously ligated with an alpha mating factor pre-pro secretion signal.

An additional embodiment of the present invention relates to fragments of both the lactoferrin gene and lactoferrin. The active sites of the lactoferrin protein are the iron-binding domains. Protein sequences which contain one or more of the iron-binding domains of the lactoferrin protein sequester iron and, therefore, are useful in the antiseptic, dietary supplement, and food-spoilage retardant embodiments of the present invention. The present invention contemplates a (DNA) fragment of the DNA molecule encoding human lactoferrin. The fragment encodes a portion of the human lactoferrin protein containing at least one of the iron-binding domains.

For example, a DNA fragment of the lactoferrin gene encoding only one iron-binding domain of human lactoferrin can be obtained through a specific design of oligonucleotides for PCR amplification or through an antibody probe screening of a cDNA library, which procedures are readily apparent to one skilled in the art. These fragments are also usefull, e.g., as intermediates in the synthesis of the full-length gene and protein.

Expression of human lactoferrin using the aforementioned modified plasmids is carried out according to techniques that will be readily apparent to the skilled artisan, such as those disclosed in Rothstein (1983) and Tschopp, et al., (1987), supra.

Purification of the expressed protein according to the present invention is preferably carried out by one of several methods. In one preferred embodiment, a cell-free culture media containing the expressed lactoferrin protein is passed through a filter that retains material having a molecular weight greater than about 10,000 daltons and then sterilizing the retained protein. The material retained by the filter is subjected to a two-step affinity chromatography process. In the first step, the affinity ligand is the reactive dye Cibacron blue F3G-A (color index (C.I.) 61211, λmax 605(374)nm) as disclosed by Bezwoda, et al., *Clin. Chim. Acta.*, 157, 89–94 (1986); and *Chemical Abstracts Service* (CAS) No. 12236-82-7, which disclosures are hereby incorporated by reference. Cibacron blue F3G-A can be covalently bound to a cross-linked agarose gel by the triazine coupling method as described by Bolme, et al., *J. Chromatography*, 69, 209–214 (1972), which disclosure is hereby incorporated by reference. In the second step, controlled-pore class (CPG) or silicic acid is used to further purify the adsorbed material obtained in the first step.

Figure 2:
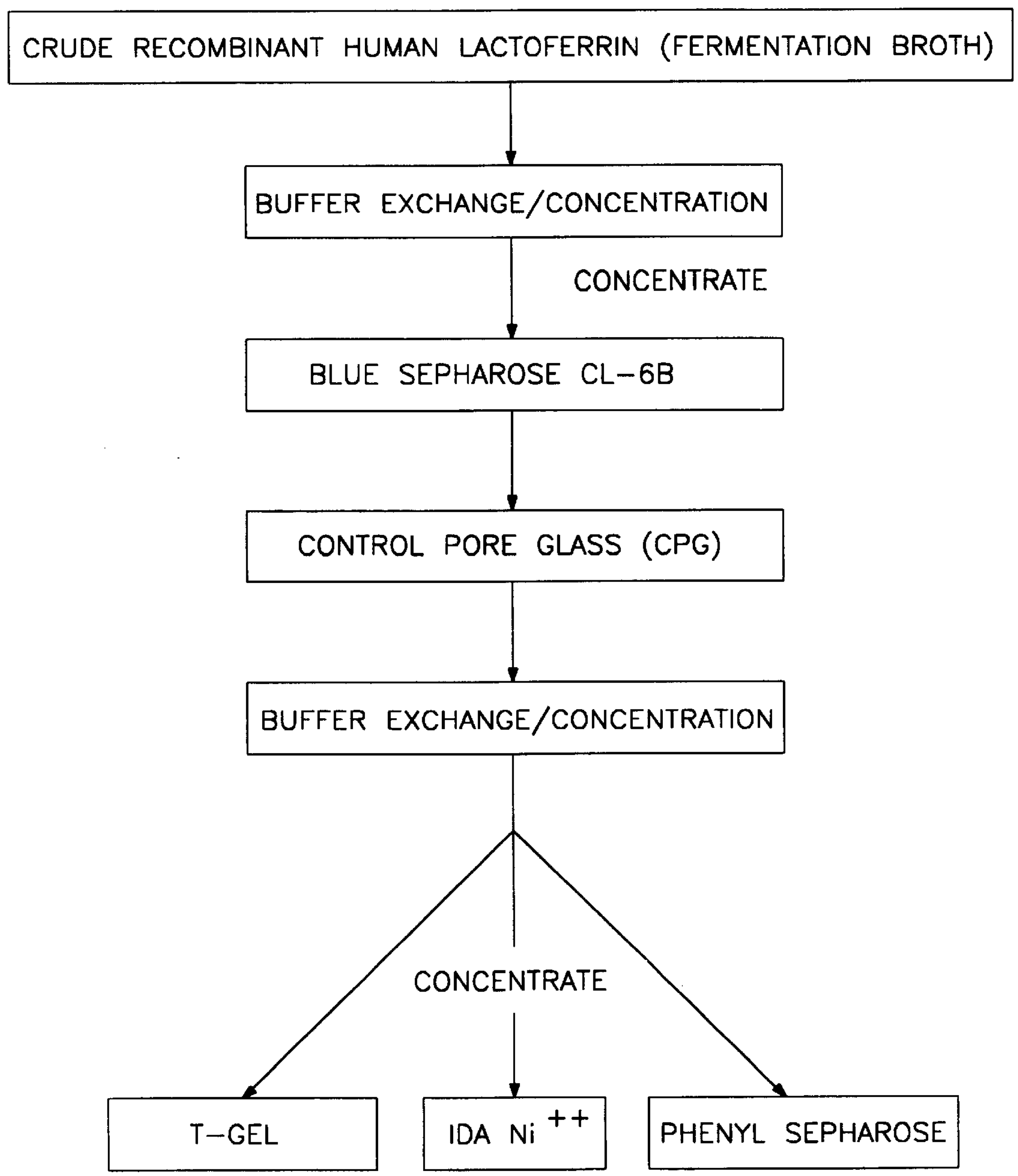
FIG. 2 is a flow chart showing the purification of lactoferrin.

In another preferred embodiment, the adsorbed material from the CPG or silicic acid is further chromatographed in a third step using one of the following chromatography techniques before final filtration and sterilization: T-Gel chromatography; immobilized metal-ion affinity chromatography (IMAC) using a metal ion capable of forming a complex with lactoferrin, such as nickel or copper, which can be coupled with an imminodiacetic acid-epoxy activated gel (IDA Me(II)) as described by Sulkowski, *Frontiers in Bioprocessing*, Sidkar et al., Ed., 343–353 (1990), which disclosure is hereby incorporated by reference; or chromatography with the ligand phenyl glycidyl ether, which can be coupled to a cross-linked agarose gel as described by Janson, et al., *Protein Purification Principles High Resolution Methods and Applications*, VSH Publishers, New York (1989), which disclosure is hereby incorporated by reference. The two-step and three-step methods previously described are schematically shown by the diagrams in FIG. 2.

The improved chromatography process of the present invention is useful in purifying proteins, such as lactoferrin produced in accordance with the present invention. As shown in FIG. 1, crude fermentation broth contained in tank 1 passes to permeable membrane 3, which retains material having a molecular weight greater than 10,000 daltons and passes an ultra filtrate containing water, salts, and low molecular-weight proteins. The retained material is washed with a buffer and further concentrated. The washed material is then applied to chromatography column 5 containing an adsorbent that has been equilibrated with the buffer used to wash the filtered material while valve 7 is open and valve 9 is closed. After non-adsorbed material is discharged through valve 7, valve 7 is closed and valve 9 opened. Adsorbed material is then eluted, and the eluate passed directly to the second column 11, containing an adsorbent previously equilibrated with the eluant used to elute the adsorbed material. Use of the same medium to elute material from the adsorbent in column 5 and equilibrate the adsorbent column 11 avoids the need for timely and involved medium exchange procedures between the two adsorption steps. Passage of the adsorbed material through column 11 occurs while valve 13 is open and valve 15 is closed. Eluting adsorbed material from column 11 occurs while valve 13 is closed and valve 15 is open, thereby passing eluate from column 11 directly to a filter (not shown) capable of retaining material having a molecular weight of at least 10,000 daltons. Although demonstrated for use in purifying lactoferrin, the aforesaid method and apparatus is contemplated in other tandem chromatography procedures that will be readily apparent to the skilled artisan. For example, the invention is useful in purifying proteins with similar hydrophobicity to lactoferrin.

The lactoferrin of the present invention having either no metal loading (iron-free lactoferrin, apolactoferrin) or a low metal loading, preferably less than 25%, more preferably less than 20%, most preferably less than 10% of the metal-binding sites occupied, by virtue of being capable of sequestering a significant amount of iron, is useful in applications to individuals where the removal of iron or other transition metals from the individual can have beneficial effects, such as in cosmetics, personal hygiene products, such as feminine douches and mouthwashes, medical and surgical devices and products, topical antiseptics, ophthalmic solutions, oral and intravenous antibiotics, immunopotentiators, antioxidant, and anti-inflammatory and anti-tumor agents.

Lactoferrin can be used as an antiseptic in accordance with the present invention either alone or in the form of a powder, solution, ointment, aerosol spray, or cream to any part of the subject as an aid in the prevention or treatment of microbial infections. By depriving the surrounding environment of iron, lactoferrin inhibits the growth of microbes, such as bacteria. Preferable antiseptics of the present invention include lactoferrin either alone or compounded with carriers such as saline, silica, talcum, stearic acid, its magnesium or calcium salt, polyethyleneglycol, and fatty emulsions and suspensions that will be readily apparent to the skilled artisan. The lactoferrin is preferably present in the antiseptic based on 1 ml of the carrier at 0.1–2 mg, preferably 0.2–2 mg. An effective amount of the lactoferrin varies depending on the individual treated, severity of infection, if any, and the area to which administration is contemplated. Preferably, in treating mammals a twice-daily administration of 0.1–2 mg, more preferably 0.5–2 mg, most preferably 1 mg, of lactoferrin per 1 square centimeter effected area is contemplated more preferably 0.1 square centimeter. Lactoferrin can be used as an antiseptic in accordance with the present invention to treat accidental scratches or burns. For example, lactoferrin is applied over the affected area in the form of a 0.1–2 weight %, preferably 0.1–1 weight % solution, or such a solution is used to impregnate a Band-Aid type bandage with lactoferrin. Lactoferrin can be used as an antiseptic in accordance with the present invention to provide prophylaxis in personal hygiene products. For example, the prevention of vaginal infections is accomplished by daily administration of 25–50 mg of lactoferrin in a form of douches or pads. Similarly, the oral infections are prevented by daily administration of 25–50 mg of lactoferrin in a form of mouthwash. Also, lactoferrin provides added protection against sexually transmitted infections when compounded into any device used during sexual activities by either males or females. For example, lactoferrin is added into lubricant to cover condoms at the concentration of 25–50 mg per application. Lactoferrin can be used as antiseptic in accordance with the present invention to impregnate any surgical tools, materials or protective clothing that is used by health care personnel. For example, surgical gloves, masks or linens are covered with a 0.1–2.0% by weight solution of lactoferrin, preferably 0.1–1% by weight. The solution can be applied by a spray, conveniently provided in pressurized aerosol cans or pump bottles.

Lactoferrin can be useful in the treatment and prevention of opportunistic bacterial, viral, and fungal infections. Opportunistic infections are caused by normally non-pathogenic organisms in patients whose host defense mechanisms have been compromised. By sequestering iron, lactoferrin inhibits the growth of these organisms, making them more susceptible to antibiotic therapy. Depending on the type of infection involved, treatment can involve one or more types of systemic (oral, nasal, intravenous, etc.) or topical administration. Examples of such infections include pneumonia, acquired immune deficiency syndrome (AIDS), candidiasis, diarrhea, and neonatal sepsis. In treating pneumonia, for example pneumonia caused by *Streptococcus pneumoniae*, antibiotics have minimal impact on mortality during the first five days of illness. By sequestering iron, lactoferrin can inhibit the growth of pneumococcals, and make them more susceptible to antibiotic therapy. Although administration by oral and intravenous routes is contemplated, a simple delivery system of lactoferrin by inhalation involving topical administration to pulmonary membranes is most preferred. Generally, treatment will involve administration three to four times daily of an aqueous solution of lactoferrin in an amount of 100–200 mg per dose for a period of time of 7 to 10 days by inhalation using a known inhaler. A particular cause of opportunistic infections is the lowered host immunity caused by AIDS. Systemic administration of lactoferrin in AIDS patients can help prevent or at least delay the onset of secondary infections. A variety of treatment modalities are contemplated. Intravenous administration of lactoferrin twice daily in an amount of 100–200 mg per injection is recommended for a period of time of one week followed by a one week break. The continuation of this pulse therapy is contemplated for a period of time of three to six months. Depending on the particular infection, an additional localized treatment is also contemplated. For example, in the case of oral candidiasis, the treatment will include administration of lactoferrin as a mouthwash twice daily in an amount of 100–200 mg per dose for a period of time of 7 to 10 days. For a pulmonary infection, such as *Pneumocistis carinii*, the treatment will involve administration of lactoferrin by inhalation four times daily in an amount of 100–200 mg per dose for a period of time of 7 to 10 days. For Kaposi's sarcoma treatment will involve topical administration of lactoferrin in an ointment, twice daily, in an amount of 50–100 mg per dose for three to four weeks. Fungi infections, depending on the type and location, are treated orally, by intravenous injection, or topical administration. For example, infections, such as vaginal candidiasis, are treated with lactoferrin in a form of douches (vaginal wash) twice daily in an amount of 100–200 mg per dose. Diarrhea, while not usually life threatening, can be dangerous, particularly in infants, because of the potential for fluid imbalance. By virtue of its high affinity for iron, lactoferrin can inhibit the growth of pathogens in the gastrointestinal tract. Treatment of diarrhea will involve oral administration of lactoferrin twice daily at an amount of 100–200 mg per dose for a period of time of 7 to 10 days. The treatment of ulcers caused by *Helicobacter pylori* is also facilitated by the use of lactoferrin. Lactoferrin will not only prevent utilization of iron by the bacteria by sequestering excessive iron from food, it will also deliver the iron to the small intestine where it is recognized by receptors specific to lactoferrin. Treatment will involve oral administration of lactoferrin twice daily in an amount of 200–400 mg per dose for a period of time of 7 to 10 days. Neonatal sepsis, which can coincide with low production levels of lactoferrin in newborn infants, is also subject to treatment by lactoferrin in accordance with the present invention, and particularly in combination with current antibacterial therapy. Treatment will include intravenous administration of lactoferrin twice daily in an amount of 100–200 mg per dose for a period of time of 7 to 10 days. In patients having burns over a large portion of the body, the plasma level of lactoferrin increases 10 to 20 times the normal amount, the body responding to injury by secreting a powerful antimicrobial agent-lactoferrin. Topical administration of lactoferrin to burn patients, by sequestering iron, will prevent development of surface infection. Treatment will involve topical administration of lactoferrin in an ointment, cream, or other topical vehicle twice daily in an amount of 50–100 mg per dose for a period of time of three to four weeks. Chronic iron overload, known as hemosiderosis, is characterized by greater than normal iron levels in certain body tissues. When associated with tissue injury, the condition is known as hemochromatosis. Lactoferrin, as the natural chelating agent for iron, offers a viable treatment for such disorders. Preferable treatment involves intravenous or subcutaneous doses of lactoferrin once daily at an amount of 300–500 mg. Lactoferrin can also be used to sequester iron implicated in heart disease. By sequestering iron that promotes the oxidation of lipids, which when oxidized can clog arteries, lactoferrin can aid in reducing heart attacks. The prophylactic treatment involves intravenous administration of lactoferrin twice weekly in an amount of 200–500 mg. The treatment is contemplated for high risk patients having high levels of cholesterol. Ischemic heart disease remains the most important cause of morbidity and mortality in the U.S. Over the last decade acute revascularization with thrombolytic drugs has emerged as the standard treatment for patients with acute myocardial infraction. Considerable evidence has emerged over the last decade which indicates that iron may play a key role in pathogenesis of reperfusion injury in the heart. Lactoferrin can sequester large amounts of iron that tend to be released following heart attacks, which thus reduces the amount of iron available for reacting with oxygen to generate free radicals, which cause damage to muscle fibers and cell walls. Preferable treatment involves intravenous administration of lactoferrin immediately after heart attack in an amount of 500–1,000 mg. The treatment of a pneumococcal, streptococcal or staphylococcal infection following trauma of the cornea is also facilitated by lactoferrin. These infections are usually primary causes of corneal ulcers. The treatment will involve topical administration of lactoferrin in an ointment, eye drops or other topical vehicle twice daily in an amount of 10–20 mg per application. Lactoferrin can also be utilized to sequester iron from contact lenses having an application in antiseptic treatment of lenses between wearing times. The effective solution will consist of 0.1–1.0% of lactoferrin in water. The treatment of tumors, such as brain tumors, can also be facilitated by the use of lactoferrin. Newly developed catherization procedures permit the delivery of lactoferrin directly to a blood supply aorta of a tumor, such as a brain tumor, which, by reducing the iron necessary for metabolism of the tumor cells, can prevent the growth of the tumor. Treatment will involve weekly administration of lactoferrin through a microcatheter in an amount of 1–2 grams per dose for a period of time of three to six months. Lactoferrin can also be used as an adjuvant in vaccination. Subunit antigens and peptides made by recombinant DNA technology are not very immunogenic, making their use as vaccines contingent upon the availability of adjuvants that are safe for use in humans and are able to augment sufficiently the immunogenicity of these molecules. Because it modulates a number of immunological responses including myeloid differentiation, modulation of macrophage-mediated cytotoxicity, and regulation of the primary antibody response, lactoferrin can be used as such an adjuvant. The lactoferrin is systemically administered at 100–200 mg per vaccination. Lactoferrin administration before, during, or after vaccination is contemplated based on the specific antigen used for the vaccine.

The nutritional supplement of the present invention contains an effective amount of lactoferrin loaded with iron, either alone or in combination with one or more nutritionally acceptable carriers or adjuvants. Preferred nutritional supplements include tablets, gelatin capsules, or liquids containing the lactoferrin together with adjuvants or diluents, such as lactose, dextrose, sucrose, mammitol, sorbitol, cellulose, and glycine; binders, such as magnesium aluminum silicate, starch, paste, gelatin, tragacanth, methylcellulose, sodium carboxymethylcellulose, and polyvinylpyrrolidone; disintegrants, such as starches, agar, alginic acid or its sodium salt, and effervescent mixtures; as well as absorbents, colorants, flavors and sweeteners. Alternatively, the iron-loaded lactoferrin can be added to foods such as baby formula, cereal, and ice cream to enhance the nutritional value of the food. The preferred amount of iron-loaded lactoferrin in the supplement based on the weight of 1 g of the supplement is 5–50 mg, more preferably 20–30 mg, and most preferably 25 mg. An effective daily amount of based on the individual, iron-loaded lactoferrin varies, from about 10–30 mg, preferably 20–30 mg, and more preferably 25 mg. Loading lactoferrin with iron is accomplished by simple titration with, e.g., ferrous ammonium in the presence of bicarbonate, according to methods that will be readily apparent to the skilled artisan. Preferred loading is such that at least about 35%, more preferably at least about 50%, and most preferably at least about 70%, of the metal binding sites are iron bound. Lactoferrin can be applied to food (either solid or liquid) to retard spoilage in accordance with the present invention either alone or compounded with any of the aforesaid nutritionally acceptable carriers or diluents. By sequestering iron, and thereby suppressing its catalytic activity, the lactoferrin reduces the iron available for either microbial multiplication or the production of potentially cell-damaging free-radicals that are formed in iron catalyzed reactions from hydrogen peroxide or superoxide. For example, the lactoferrin is particularly useful in inhibiting rancidity in meat, which is iron-dependent lipid peroxidation. To inhibit microbial growth, particularly in liquid foods such as beer and wine, the lactoferrin can be added directly to the liquid or used to coat filters through which the liquid food passes during processing. An effective amount of the lactoferrin for retarding spoilage varies depending on the type and amount of food contemplated. Preferably, the amount of lactoferrin applied to food in accordance with the present invention varies from 0.1–1 mg/ml of food with which it is mixed, or based on the surface area of the filter or solid food to which it is applied from 0.1–1 mg/cm$^2$. The preferred amount of lactoferrin compounded with a carrier in a food additive for retarding spoilage varies based on 1 ml of the carrier from 0.1–2 mg, preferably 0.2–2 mg.

The antiseptic, dietary supplement, and food-spoilage retardant of the present invention can be sterilized and/or contain adjuvants, such as preserving, stabilizing, wetting or emulsifying agents, solution promoters, salts for regulating osmotic pressure and/or buffers. In addition,they may also contain other therapeutically valuable substances. Said compositions are prepared according to conventional mixing, granulating, and coating methods.

The lactoferrin contemplated for use in accordance with the present invention is preferably of human origin, more preferably via DNA recombinant means, but other lactoferrins, such as natural bovine, goat and porcine lactoferrin, isolated and purified using methods applicable to natural human lactoferrin, are contemplated.

The following non-limiting examples are provided to illustrate the present invention. All parts and percentages are by weight unless indicated otherwise.

EXAMPLE 1

Cloning and Expression of Lactoferrin

Human lactoferrin is obtained from a genetically altered organism. Using breast tissue excised during the mastectomy of a woman during the eighth month of pregnancy, a human mammary gland genomic library is prepared according to the procedure of Gubler, et al., *Gen.*, 40, 1–8 (1983), which disclosure is hereby incorporated by reference. A human mammary gland genomic library of cDNA ligated to λgt11 is available from Clontech, Calif. The library is transferred onto agar plates containing a high density of *E. coli* Y 1090 (Clontech, Calif.) (5×10$^4$ plaques per 90 mm plate or 1.4×10$^5$ plaques per 150 mm plate). The plates are allowed to stand for 3.5 hours at 42° C. to obtain a lytic growth of the phage. The plates are thereafter overlaid with nitrocellulose filters (Schleiher and Scimell Inc., Wouburn, Mass., under no. BA 85 NC) and heated in an incubator at 37° C. for 3.5 hours.

Positive clones (i.e., containing the cDNA) are identified on the membranes using rabbit antibody to natural human lactoferrin purified in accordance with Example 9 described hereafter. Nitrocellulose filters are removed from the plates after plaque transferral, and coated with the antibody purified as described under Example 9, which hybridizes with positive plaques. Following removal of excess antibody, positive plaques are developed by first applying an anti-rabbit IgG conjugated with biotin (Sigma Chemical Co., St. Louis, Mo.), and then, following removal of excess biotin conjugate, applying avidin conjugated with horse radish peroxidase (Sigma Chemical Co., St. Louis, Mo.). Finally, the positive plaques are identified in the reaction catalyzed by horse radish peroxidase using as an enzyme substrate 4-chloro-1-Naphtol.

The positive plaques are then used to infect *E. coli* Y 1090 to produce large amounts of phage in accordance with procedures set forth in Davis, et. al. (1986), supra. The resulting bacteriophage is purified using 10% polyethylene glycol and DNA is isolated from the phage according to the procedures disclosed in Kislow, *N.A.R.*, 14, 6767 (1986), which disclosure is hereby incorporated by reference. Following the procedures in Davis, et al. (1986), supra, the cDNA insert encoding lactoferrin is sub-cloned as follows: the cDNA insert is cut out from the phage DNA using EcoR I and purified using a high resolution ion-exchange chromatography column (GEN-PAK™ Fax, Millipore Corporation, Waters Chromatography Division, Milford, Mass.). The thus purified cDNA insert is ligated using T4 DNA ligase into plasmid pGEM-4 (Promega, Madison, Wis.) as described by Yanish-Perron et al., *Gen.*, 33, 103–109 (1985), which disclosure is hereby incorporated by reference that has been cut using EcoR I using standard techniques. The plasmid containing the insert is then transferred into *E. coli* JM109 (Promega, Madison, Wis.) as described by Hanahan, *J. Mol. Blot.*, 166, 557 (1983), which disclosure is hereby incorporated by reference. The bacteria are transferred to agar plates containing ampicillin and the positive colonies grown. The plasmid is then isolated and the cDNA insert is cut from the plasmid using EcoR I and purified by ion exchange chromatography as described above.

The cDNA insert is then ligated into the *Pichia pastoris* expression vector pAO804, so as to be flanked by the 5' and 3' regulatory sequences of the methanol-induced alcohol oxidase gene (AOX1) of *P. pastoris* in accordance with the procedures described by Sreekrishna, et al., *Biochemistry*, 28, 4117–4125 (1989); and Rothstein, *Methods in Enzymology*, 101, 202–210 (1983), which disclosures are hereby incorporated by reference. The resulting vector is then transformed into *Pichia pastoris* GTS115 (His4) by the method of spheroplast as described by Creeg, et al., *Mol. Cell. Biol.*, 5, 3376–3385 (1985), which disclosure is hereby incorporated by reference. The selected transformant cells are grown in 10 ml buffered minimal glycerol-complex medium at 30° C. with shaking for three days. The saturated culture is centrifuged for 10 minutes at 3000 G. The cell pellet is resuspended with 2 ml of buffered minimal methanol-complex medium and returned to the 30° C. shaker for another three days. Cells are pelleted by centrifugation and both the pellet and supernatant are analyzed for the presence of lactoferrin. Alternatively, the procedure of Hagenson et al., *Enzyme Microb. Technol.*, 11, 650–656 (1989), which disclosure is hereby incorporated by reference, is followed to grow the cells in a fermentor up to $OD_{600}$ of about 1.0 then harvested, and washed with and suspended in minimal methanol media at an $OD_{600}$ about 4.0. The culture is held at 30° C. while maintained at a pH of 5.0 by adding $NH_3$ gas to the air stream. Expressed lactoferrin is recovered from the supernatant of the fermentation media following 15 minutes centrifugation at 5000 rpm using a Beckman J-21B with a Rotor JA 14.

EXAMPLE 2

Concentration and Initial Purification of Lactoferrin

One liter of the supernatant from Example 1 is adjusted to about 40C and filtered under pressure through a polysulfone ultrafiltration membrane having a pH operating range of 1–14 on a polypropylene mesh support (PELLICON™ Cassette filter System assembled with Procon pump and PTGC membrane, Millipore Corporation, Milford, Mass.) to retain proteins in excess of about 10,000 molecular weight. Pressure with simultaneous circulation is applied until 900 ml of ultra filtrate is collected. A flow rate of about 100 ml per minute is maintained during the filtration process. The retained material (100 ml) is diluted with 900 ml 20 mM phosphate buffer (pH 7.4) and re-filtered, which is repeated four times (final exchange ratio=10,000). The final material retained is sterilized (0.22 micron GELMAN™ filter).

EXAMPLE 3

Purification of Lactoferrin using Affinity Chromatography

Human lactoferrin is purified using affinity chromatography in which the affinity ligand is the reactive dye Cibacron blue F3G-A. The sterilized material obtained in Example 2 is adjusted to a pH of 7.5 and a final concentration of sodium chloride of 0.5 M. This material is then applied onto a column (5 cm×35 cm) packed with cross-linked agarose coupled to the dye (Pharmacia Fine Chemicals, Uppsala, Sweden, BLUE SEPHAROSE™ CL-6B) and previously equilibrated with 50 mM N-[2-hydroxyethyl]piperazine-N'-[2-ethanesulfonic acid] (HEPES) buffer (pH 7.5) containing 0.5 M sodium chloride. Adsorption is performed at a flow rate of 1 ml/min followed by washing the column with 2 bed volumes of the same HEPES buffer. The non-adsorbed fraction is discarded and the adsorbed fraction containing lactoferrin is eluted from the column bed using 2 bed volumes of 50 mM HEPES buffer (pH 7.5) containing 1 M sodium chloride.

EXAMPLE 4

Purification of Lactoferrin using Control Pore Glass (CPG) Chromatography

Human lactoferrin is purified using control pore glass (CPG) chromatography. The eluate from Example 3 is applied onto a column (1.2 cm×10 cm) packed with CPG beads (CPG 00350, ElectroNucleonics, Fairfield, N.J.) and previously equilibrated with 50 mM HEPES buffer (pH 7.5) containing 1 M sodium chloride. Adsorption is performed at a flow rate of 1 ml/min followed by washing the column with 2 bed volumes of the same buffer. The non-adsorbed fraction is discarded, and the adsorbed fraction is eluted with 2 bed volumes of 0.25 M tetraethylammonium chloride (TMAC, pH 7.5). The eluate is filtered on a membrane capable of excluding material having a molecular weight greater than 10,000 daltons (AMICON™ YM 10). The filtered material is then sterilized (0.22 micron GELMAN™ filter) and frozen at −200C.

EXAMPLE 5

Purification of Lactoferrin using Immobilized Nickel Ion Affinity Chromatography Human lactoferrin is purified using immobilized metal ion affinity chromatography (IMAC). An imminodiacetic acid-epoxy activated gel (Pharmacia Fine Chemicals, Uppsala, Sweden, CHELATING SEPHAROSE™ 6B) is washed with water and equilibrated with 0.1 M sodium acetate buffer (pH 4.0) containing 1 M sodium chloride. The gel is then packed into a chromatographic column (1.2 cm×10 cm) and saturated with 4 bed volumes of the same sodium acetate buffer further containing 5 mg/ml of nickel chloride. Excess metal is washed from the column with the sodium acetate buffer, and the gel is equilibrated with 20 mM HEPES buffer (pH 7.0) containing 1 M sodium chloride and 2 mM imidazole.

The product of Example 4 is mixed with HEPES, sodium chloride, and imidazole to obtain a pH of 7.0, 20 mM HEPES, 1 M sodium chloride, and 2 mM imidazole. The mixture is applied onto the column at a flow rate of about 1 ml/min followed by,washing the gel with 2 bed volumes of 20 mM HEPES buffer (pH 7.0) containing 1 M sodium chloride and 2 mM imidazole. The non-adsorbed fraction is discarded, and the adsorbed fraction containing lactoferrin is eluted using 2 bed volumes of 20 mM HEPES buffer (pH 7.0) containing 1 M sodium chloride and 20 mM imidazole.

EXAMPLE 6

Purification of Lactoferrin using Immobilized Copper Ion Affinity Chromatography Human lactoferrin is purified using immobilized metal ion affinity chromatography (IMAC). An imminodiacetic acid-epoxy activated gel (Pharmacia Fine Chemicals, Uppsala, Sweden, CHELATING SEPHAROSE™ 6B) is washed with water and equilibrated with 0.1 M sodium acetate buffer (pH 4.0) containing 1 M sodium chloride. The gel is then packed into a chromatographic column (1.2 cm×10 cm) and saturated with 4 bed volumes of the same sodium acetate buffer further containing 5 mg/ml of copper sulfate. Excess metal is washed from the column with the sodium acetate buffer, and the gel is equilibrated with 50 mM TRIS-HCL buffer (pH 8.0) containing 1 M sodium chloride.

Lactoferrin equilibrated to 50 mM TRIS-HCL pH 8.0, 1 M NaCl is applied onto the column at a flow rate of about 1 ml/min followed by,washing the gel with 2 bed volumes of 50 mM TRIS-HCL buffer (pH 7.0) containing 1 M sodium chloride. The non-adsorbed fraction is discarded, and the adsorbed fraction containing lactoferrin is eluted using 2 bed volumes of 200 mM sodium acetate buffer pH 3.0.

EXAMPLE 7

Purification of Lactoferrin Using T-Gel Affinity Chromatography

Human lactoferrin is purified using T-gel affinity chromatography. T-gel adsorbent is prepared according to the procedure described by Porath, et al., *Methods in Enzymology*, 44, 19–45 (1976), which disclosure is hereby incorporated by reference, and packed into a column (1.2 cm×10 cm). The final product of Example 4 is adjusted to a pH of 7.5 and a final concentration as follows: 50 mM PIPES buffer (piperazine-N,N'-bis[2-ethanesulfonicacid] and 1,4-piperazinediethanesulfonicacid) buffer and 0.7 M ammonium sulfate. The adjusted material is applied on the column that has been previously equilibrated to 50 mM PIPES buffer (pH 7.5) containing 0.7 M ammonium sulfate with a flow rate of about 1 ml/min. The non-adsorbed fraction containing lactoferrin is adjusted to a concentration of 0.1 M ammonium sulfate and then applied to an identical T-gel column previously equilibrated to 50 mM PIPES buffer (pH 7.5) containing 1.0 M ammonium sulfate. The column is then washed with 7–8 bed volumes of 50 mM PIPES buffer (pH 7.5) containing 1.0 M ammonium sulfate, with lactoferrin being present in the non-adsorbed fraction.

EXAMPLE 8

Purification of Lactoferrin Using Hydrophobic Interaction Chromatography

Human lactoferrin is purified using hydrophobic interaction chromatography on a cross-linked agarose gel coupled to phenyl glycidyl ether (PHENYL SEPHAROSE™ CL-4B, Pharmacia Fine Chemicals, Uppsala, Sweden). The gel is packed into a column and equilibrated to 50 mM PIPES buffer (pH 7.0) containing 1 M ammonium sulfate. The product of Example 4 is adjusted to the equilibrating buffer and applied onto the column at a flow rate of 1 ml/min. The non-adsorbed fraction is discarded and the adsorbed fraction containing lactoferrin is eluted using 2 bed volumes of 50 mM PIPES buffer (pH 7.0).

EXAMPLE 9

Purification of Anti-Lactoferrin Serum

Anti-lactoferrin serum is purified by affinity chromatography. The adsorbent substrate for affinity chromatography is prepared by cyanogen bromide activation as described by Axen et al., *Nature*, 214, 1302–1304 (1967), which disclosure is hereby incorporated by reference. The substrate (Pharmacia Fine Chemicals, Uppsala, Sweden, CNBR-SEPHAROSE™ 4B) is coupled to human lactoferrin, which acts as the affinity ligand, as follows. One gram of substrate is swelled with 1 mM HCl and washed with the same solvent on a sintered glass filter. Ten mg of natural human lactoferrin (Sigma Chemical Co., St. Louis, Mo.) is dissolved in 0.1 M $NaHCO_3$ buffer (pH 8.3) containing 0.5 M sodium chloride (coupling buffer). The resulting solution is mixed with the washed substrate gel for 2 hours, and then mixed with 0.2 M glycine buffer (pH 4.0) for 2 hours. The gel is then washed with coupling buffer, followed by 0.1 M acetate buffer (pH 4.0) containing 0.5 M sodium chloride, followed again by coupling buffer to form the adsorbent. The adsorbent is packed into a column and washed with 20 mM phosphate buffer (pH 7.4) containing 0.5 M sodium chloride. Anti-lactoferrin serum obtained from an inoculated rabbit (Sigma Chemical Co., St. Louis, Mo.) is passed through the column at a flow rate of 1 ml/min and the non-adsorbed material discarded. Adsorbed material containing the purified protein is eluted with 2 bed volumes of 0.2 M glycine buffer (pH 2.0) containing 0.5 M of sodium chloride. The eluate is neutralized with 0.1N NaOH to obtain pH 7.5 and then sterilized (0.22 micron GELMAN™ filter) and frozen at −20° C.

EXAMPLE 10

Cloning of Human Lactoferrin Gene by PCR

The human lactoferrin gene is cloned by PCR amplification from a human mammary gland library in λgt11. Phage DNA is prepared from the library by using standard procedures described in Maniatis (1989), supra. Oligonucleotide primers are prepared to the 5'- and 3'-ends of the gene based on the sequence published by Powell, et al. (1990), supra. The 5'-oligo is designed to begin at the coding sequence for the first glycine of the mature lactoferrin protein as defined by Powell, et al. (1990), supra, and the 3'-oligo included the lactofeltin stop codon and 21 nucleotides beyond. These oligonucleotides are prepared on an Applied Biosystems DNA synthesizer Model 380A and were obtained from Roswell Park Cancer Institute, Buffalo, N.Y. Each oligo also created a restriction endonuclease recognition site, the 5'-oligo contained a BamH I site and the 3'-oligo an Xba I site. The sequences of these oligonucleotides are given below:

```
                                         (Seq. ID No.3)
5'-oligo AGCGGATCCGGCCGTAGGAGAAGGAGTGTTCAGTGG
            BamHI

                                         (Seq. ID No.4)
3'-oligo CGATCTAGATTACTTCCTGAGGAATCCACAGGC
 XbaI
```

Figure 4:
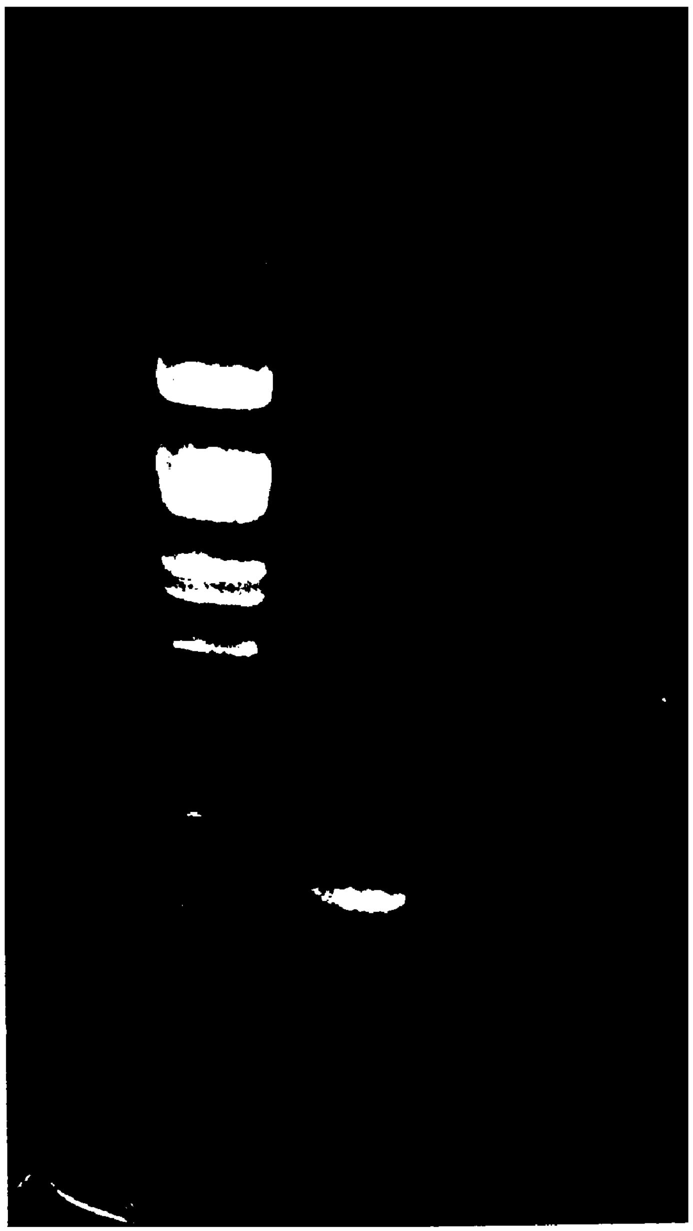
FIG. 4 is an agarose gel analysis of amplified cDNA coding human lactoferrin.
Figure 5:
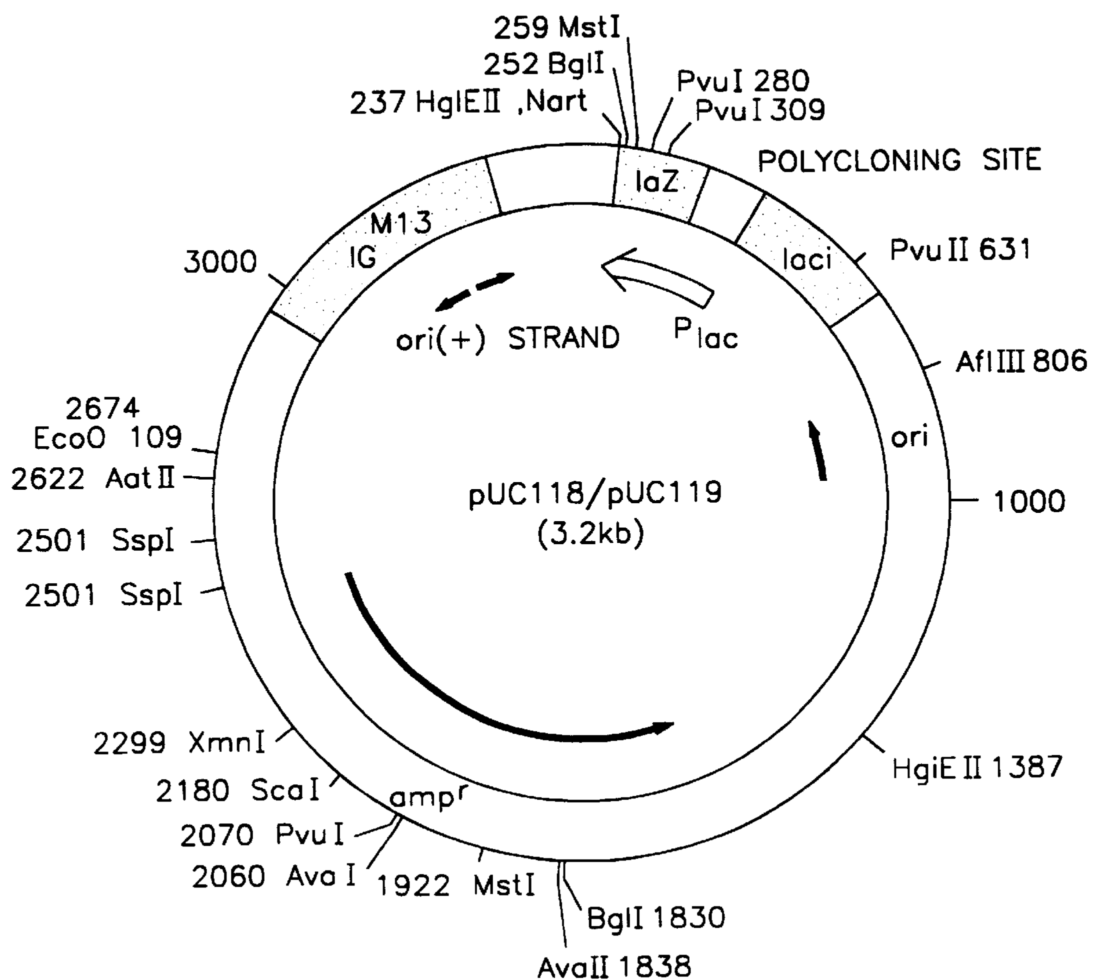
FIG. 5 is a map of the pUC118 plasmid.
Figure 6:
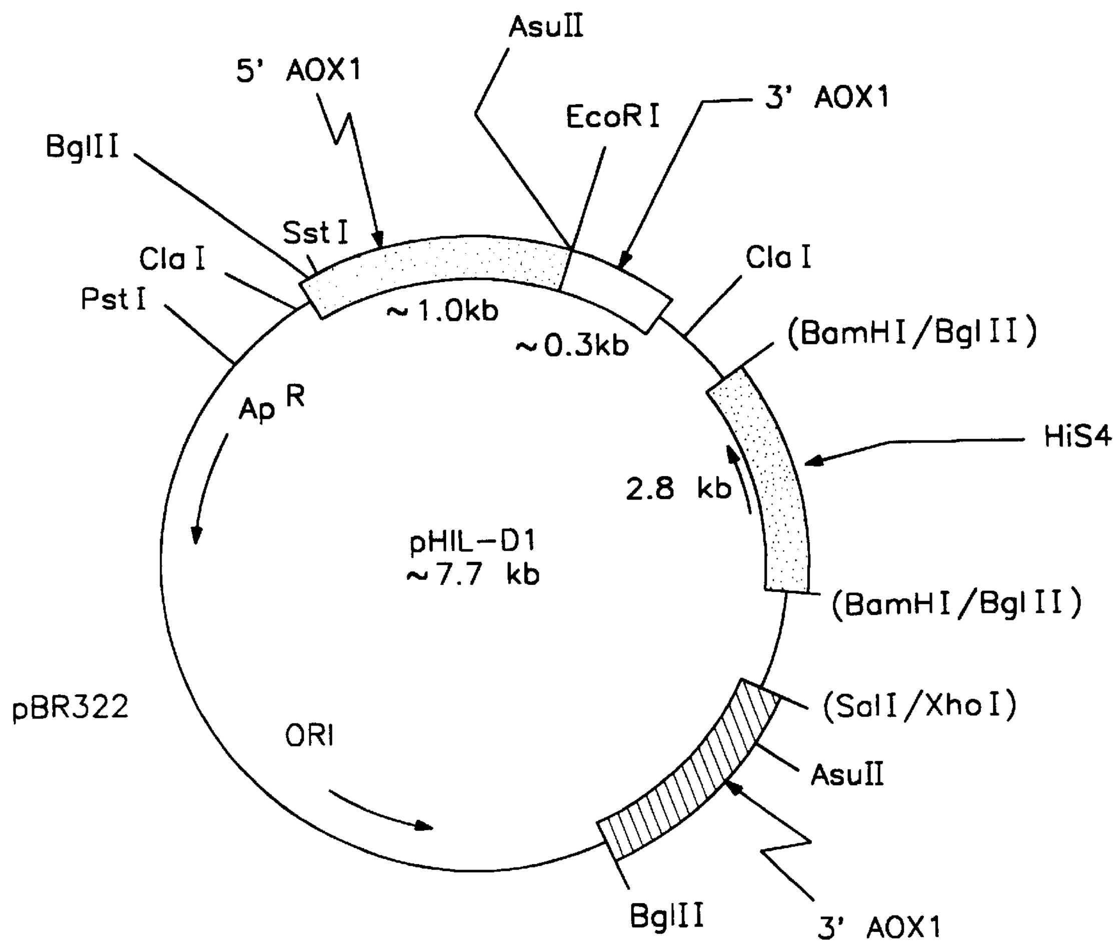
FIG. 6 is a map of the pHIL-D1 plasmid.
Figure 7:
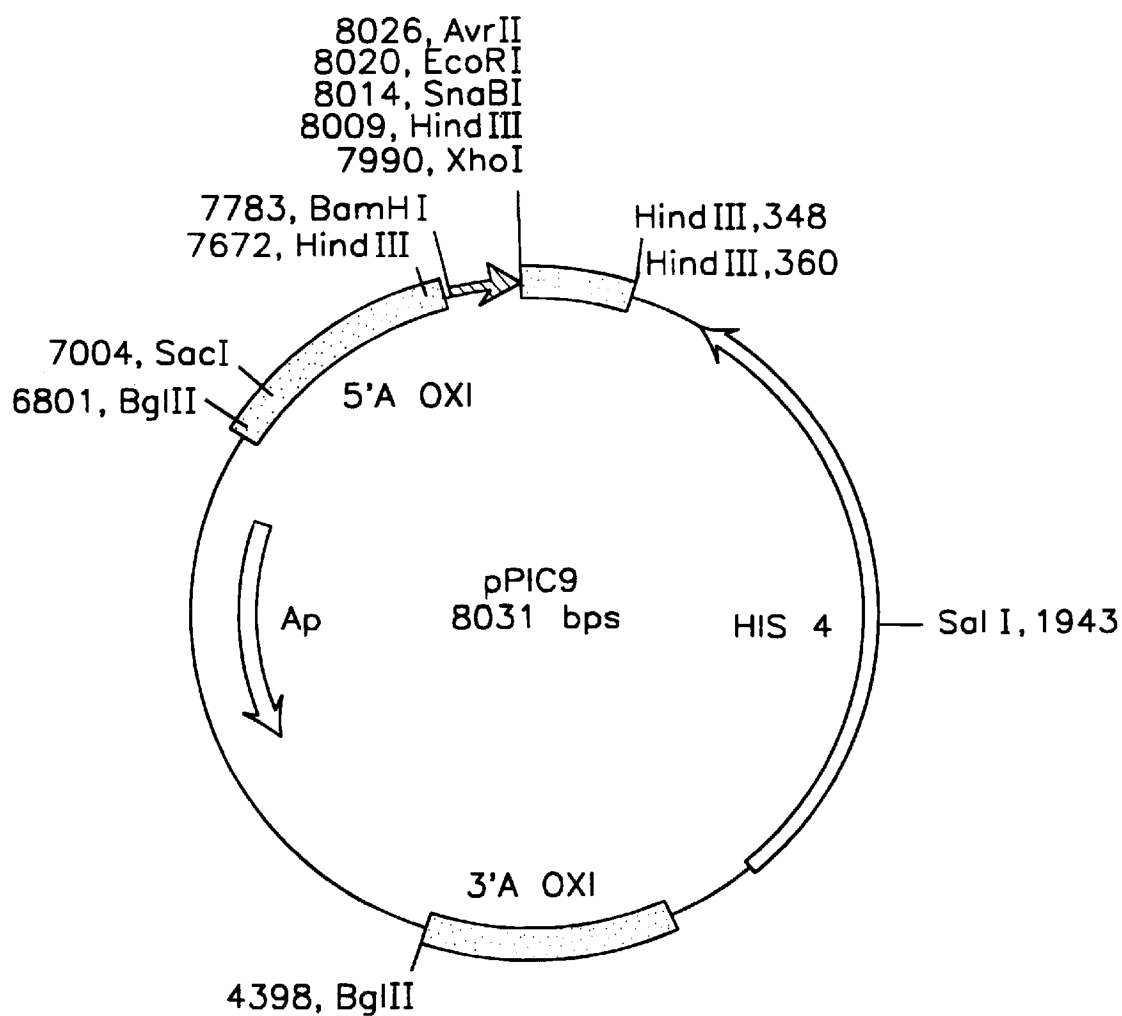
FIG. 7 is a map of the pPIC9 plasmid.

PCR amplification of the cDNA library using these oligonucleotide primers is performed with a temperature cycler (Genetic Thermal Cycler, Precision Scientific), utilizing Tag polymerase. Amplification conditions are: 1.5 min. 94° C., 2 min. 50° C., 5 min. 60° C. for 35 successive cycles PCR amplification of the cDNA library resulted in production of a 2 kbp product, which is not observed when either primer is used alone, as shown by agarose gel analysis in FIG. 4 (molecular mass markers are indicated at the left of the figure).

EXAMPLE 11

Restriction Map and Sequencing of Lactoferrin Gene

Figure 8:
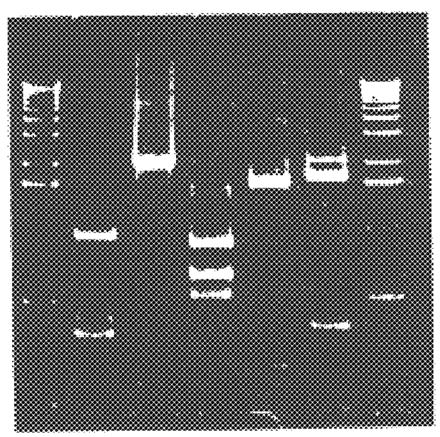
FIG. 8 is a restriction fragment map of the cDNA lactoferrin gene.

The PCR amplified fragment is cut with restriction enzymes BamH I and Xba I and following agarose gel purification is ligated into plasmid pUC 118 and transformed into *E.coli* JM101. A large amount of plasmid DNA is prepared for restriction enzyme digestion and sequencing. The cDNA lactoferrin insert is cut out with BamH I and Xba I and after agarose gel purification is subjected to digestion with the following restriction enzymes: Bgl I, HgiA I, Pvu II, and Stu I. The digestion is carried out at 37° C. for two hours. Size of the DNA fragments is determined in 2% agarose gel and is shown here as FIG. 8. FIG. 8 is a restriction fragment map of the cDNA lactoferrin gene. The top diagram shows the predicted digestion pattern, while the bottom gel illustrates the size of fragments obtained during digestion. Lanes 1 and 7 show molecular mass markers, lane 3 shows the insert encoding the lactoferrin gene, and lanes 2, 4, 5, and 6 show digestion of the insert with restriction of the enzymes Bgl I, HgiA I, Pvu II and Stu I, respectively. The digestion of cDNA lactoferrin with restriction enzymes Bgl I, HgiA I and Pvu II generate fragments which follow the pattern of a full length lactoferrin clone. Digestion with Stu I generates two (rather than the predicted three) fragments due to methylation of the DNA sequences which overlap the recognition sequence of the restriction endonuclease.

The cDNA insert encoding the human lactoferrin gene is sequenced in multiple directions using the dideoxy termination method of Sanger, *Proc. Nat. Acad. Sci. USA*, 74, 5463–5467 (1977), which disclosure is hereby incorporated by reference. Oligomers of 18 bases corresponding to the sequence of 250, 502, 751, 1003, 1252, 1502, and 1751 residues were made and used as primers. The nucleotide sequence (Seq. ID No. 1) of the instant clone is shown in FIG. 3.

EXAMPLE 12

Construction of Plasmids pUC118-LF and pUC118-LFS

The PCR product of Example 10 is digested with BamH I and Xba I, isolated from a 0.7% low melting agarose and ligated into pBlueScriptKS+ (Strata gene Corp.), which is digested with the same restriction enzymes. The resulting plasmid is designated pBSlacto. The lactoferrin gene containing fragment is then cut out from pBSlacto using Hind III and Sst I and subcloned into pUC118, which is also cut with these enzymes. The resulting plasmid is named pUC118-LF and contains the mature lactoferrin gene, that is the nucleotide sequence (Seq. ID No. 1, FIG. 3) encoding the mature lactoferrin protein (Seq. ID No. 2, FIG. 3).

To allow secretion of the lactoferrin protein, the signal sequence is added to the 5'-end of the clone using synthetic oligonucleotides based on the signal sequence published by Powell, et al. (1990), supra. The oligonucleotides used are shown below:

```
Lacto signal I:                    (Seq. ID No.5)
A
AGCTTATGAAACTTGTCTTCCTCGTCCTGTTCTTCCTCGGG
     Hind III

Lacto signal II:                   (Seq. ID No. 6)
GATCCAGCCAGAGAGAGTCCGAGGGCCCCGAGGAA
     BamHI
```

The Lacto signal I contains a Hind III restriction site and the first 12 codons including the initial methionine. Lacto signal II contains a BamH I restriction site and the final 10 codons of the signal peptide sequence. The final 9 nucleotides of two oligos are complementary and are annealed, filled-in with the Klenow fragment of DNA polymerase I from *E. coli*. The resulting double-stranded DNA fragment is digested with Hind III and BamH I and ligated into pUC118-LF, which is similarly digested. The resulting plasmid, pUC118-LFS, contains a signal sequence with the natural lactoferrin sequence.

EXAMPLE 13

Construction of Expression Plasmid pHIL-D1-LFS

Plasmid pUC118-LFS of Example 12 is digested with Hind III and Xba I and the digested DNA is filled in with Klenow DNA polymerase to produce blunt ends. The LF gene with the signal sequence (LFS) is gel purified and ligated to pHIL-D1 cut with EcoR I and blunt ended. pHILD1-LFS with the correct orientation is identified by screening quick plasmid DNA preps for correct orientation by Stu I digestion. In the correct orientation fragments of size 3.856 Kb and 5.84 Kb are expected. In the wrong orientation fragments of sizes 2.23 Kb and 7.46 Kb are expected. Several clones (>12) in the correct orientation are obtained, pooled, and used for Pichia transformation. In pHILD1-LFS the 5' untranslated region is as follows:

. . . ATTATTCGAAACGAGGAATTAGCTTATG (Seq. ID No. 7). The nucleotide composition of −1 to −25 position is AT:GC=68:32, which is in the preferred range for Pichia expression.

Plasmid pHILD1-LFS is divided into two portions. One part is cleaved with Sac I (to direct integration into the AOX1 locus of Pichia strain KM71 [aox1::ARG4, His4]) and the other part is cleaved with Sal I (to direct integration into His4 locus of KM71). Approximately 240 His+ transformants are obtained with Sac I cut DNA, and approximately 120 His+ transformants are obtained with Sal I cut DNA.

EXAMPLE 14

Construction of Expression Plasmid pPIC9-LF using Alpha Mating Factor AMF

Plasmid pPIC9 (Phillips Petroleum Co., Bartlesville, Okla.) is cut with Not I restriction enzyme and alkaline phosphatase treated. Next it is cut with Xho I restriction enzyme. The vector fragment is purified on agarose gel to separate it from the small Xho I-Not I fragment (approx. 43 bp). The purified vector is ligated with alpha mating factor, which is the following 11-mer synthetic oligonucleotide, in which only the top strand is kinased.

(P-TCGAGAAAAGACTTTTCTCCGG-OH) (Seq. ID No. 8)

The pPIC9 vector fragment linked with the 11-mer oligonucleotide is gel purified to separate it from excess 11-mer oligonucleotides. The resulting gel-purified linked vector fragment, which has Xma III and Not I ends, is ligated with the gel-purified Xma III fragment containing the mature lactoferrin gene from Example 13 (Xma III end is compatible with Not I end, thus the Xma III fragment can ligate into the Xma III/Not I ends of the vector). The resulting vector is transformed into *Pichia pastoris* GTS 115 (His4) (Phillips Petroleum Co., Bartlesville, Okla.) by the method of spheroplast. The selected transformant cells are used for expression of lactoferrin in a shake flask experiment.

EXAMPLE 15

Expression, Purification and Characterization of Human Lactoferrin from *Pichia pastoris*

The selected transformant cells from Example 14 are grown to saturation in 10 ml of buffered minimal glycerol-complex medium in a 50 ml plastic tube in a 30° C. shaker at 300 revolutions/min. for three days. The saturated culture is centrifuged for 10 minutes at 3,000 G. The cell pellet is resuspended with 2 ml of buffered minimal methanol complex medium and returned to the 30□C shaker for another three days. The supernatant is analyzed for presence of lactoferrin by SDS-PAGE and Western Blot. Lactoferrin is isolated and concentrated from the growth media in one step chromatography. Epoxy agarose is saturated with copper-ions ($CuSO_4$, 5 mg/ml), washed with 50 mM Tris-HCl buffer, pH 8.0. About 200 mg of gel is used for adsorption of lactoferrin from 1 ml of expression medium. The gel is washed with 10 ml of equilibration buffer and lactoferrin is recovered from the gel with 1 ml of 0.2 M ammonium-acetate buffer, pH 3.0.

After lyophilization, proteins are dissolved in 50 ml of SDS sample buffer. SDS-PAGE electrophoresis is performed on 9% acrylamide gels according to Laemmli, U.K., (1970) *Nature* 227, 680–685, the disclosure of which is incorporated by reference herein, and silver stained. After SDS-PAGE electrophoresis, proteins are transferred to nitrocellulose filters with semi-dry transferring apparatus. The filters are blocked overnight with 5% non-fat dry milk in 50 mM Tris HCl buffer, pH 8.0. After a brief washing with 50 mM Tris-HCl buffer, pH 8.0, filters are incubated with rabbit monospecific polyclonal anti-lactoferrin antibodies (1:20,000 dilution) for 2 hr at room temperature, washed four times with 50 mM Tris-HCl, 0.15 M NaCl, 0.05% Tween buffer, pH 8.0, and incubated for 30 min. with protein A conjugated to a horseradish peroxidase. The washes are repeated; the filters are incubated with a chemiluminescent detection kit for 1 min. and exposed to Kodak X-ray film for 1 min.

Figure 9:
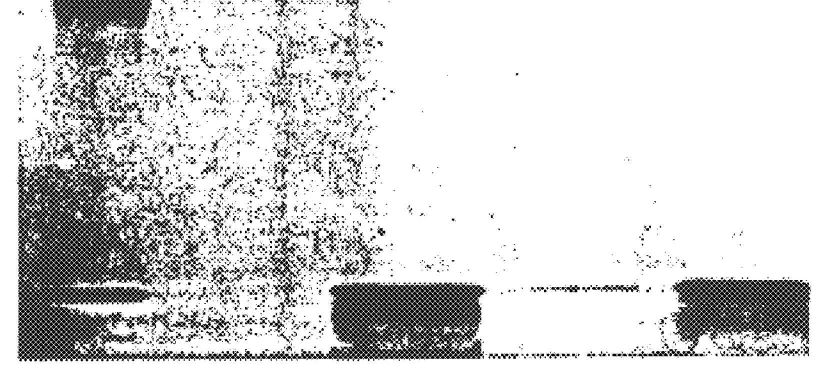
FIG. 9 is an SDS-PAGE analysis of recombinantly expressed lactoferrin according to the present invention.
Figure 10:
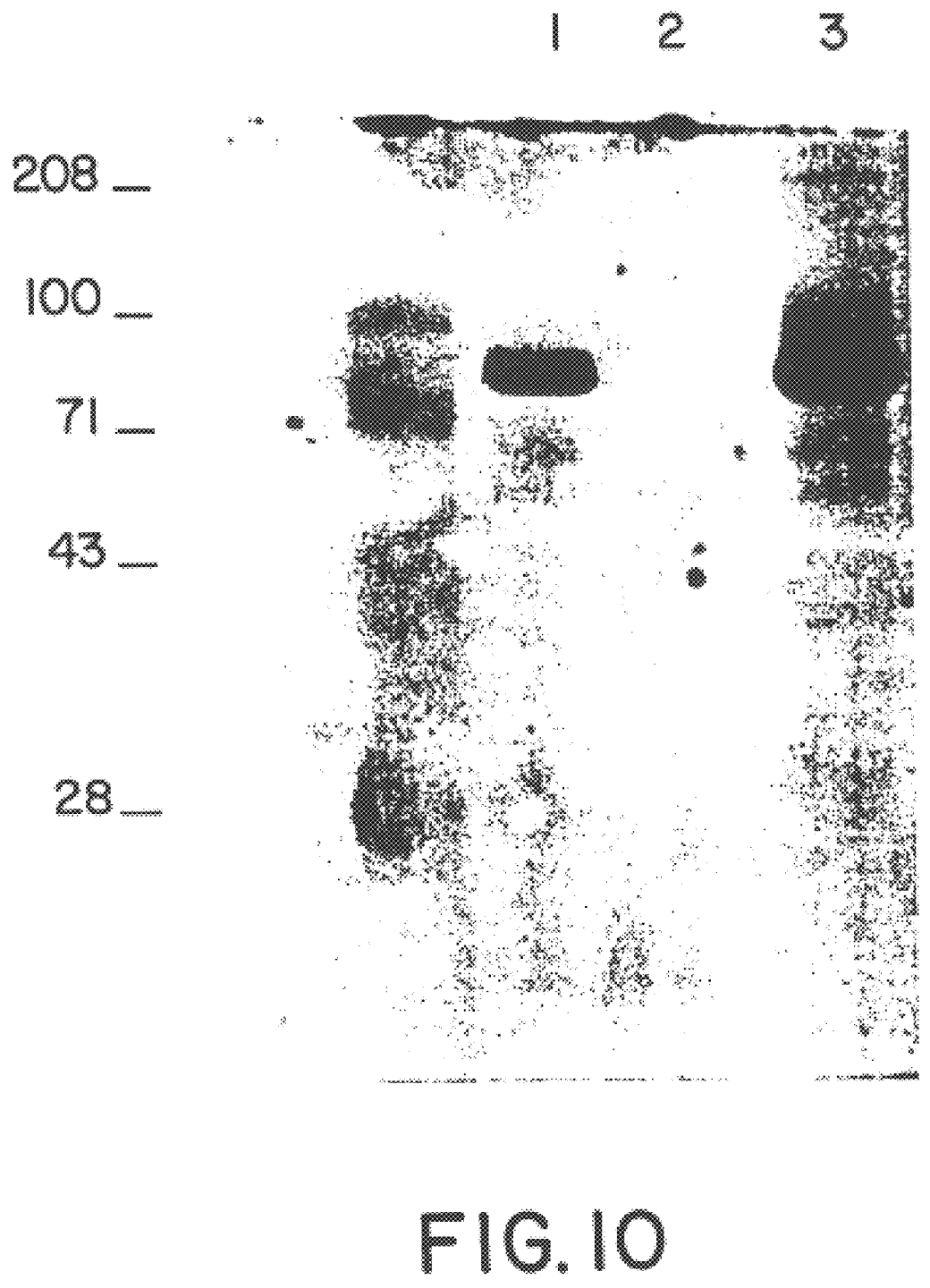

FIG. 9 shows the SDS-PAGE analysis (elution from $Cu^{++}$-epoxy agarose) of the thus recovered lactoferrin in lane 4 compared to native lactoferrin from human milk as a positive control in lane 2 and a negative control in lane 3 (medium pass through $Cu^{++}$-epoxy agarose). FIG. 10 shows the western blot analysis (elution from $Cu^{++}$-epoxy agarose) of the thus recovered lactoferrin in lane 3 compared to native lactoferrin from human milk as a positive control in lane 1 and a negative control in lane 2 (medium pass through $Cu^{++}$-epoxy agarose). Molecular mass markers (in kDa) are indicated at the left of FIGS. 9 and 10. The results show that the expressed lactoferrin is substantially identical to native human milk lactoferrin in terms of molecular mass and recognition by anti-lactoferrin antibody.

What is claimed is:

1. Recombinant lactoferrin comprising the amino acid sequence shown as SEQ ID NO:2.

2. A process for inhibiting microbial growth in a mammal comprising administering a therapeutically effective amount of the lactoferrin of claim 1.

* * * * *